United States Patent
Potnis et al.

(10) Patent No.: US 10,744,739 B2
(45) Date of Patent: Aug. 18, 2020

(54) MULTI-LAYERED STRUCTURE AND ARTICLES FORMED THEREFROM HAVING IMPROVED SPLASH RESISTANCE BY INCREASED INTERLAYER SPACING

(71) Applicant: O&M Halyard, Inc., Mechanicsville, VA (US)

(72) Inventors: Prasad Shrikrishna Potnis, Johns Creek, GA (US); Christena Nash, Alpharetta, GA (US); Eric C. Steindorf, Roswell, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 0 days.

(21) Appl. No.: 16/092,497

(22) PCT Filed: Apr. 11, 2017

(86) PCT No.: PCT/US2017/026908
§ 371 (c)(1),
(2) Date: Oct. 10, 2018

(87) PCT Pub. No.: WO2017/184378
PCT Pub. Date: Oct. 26, 2017

(65) Prior Publication Data
US 2019/0126585 A1  May 2, 2019

Related U.S. Application Data

(60) Provisional application No. 62/325,712, filed on Apr. 21, 2016.

(51) Int. Cl.
*B32B 3/30* (2006.01)
*B32B 5/02* (2006.01)
(Continued)

(52) U.S. Cl.
CPC ............ *B32B 3/30* (2013.01); *A41D 13/11* (2013.01); *A41D 13/1209* (2013.01);
(Continued)

(58) Field of Classification Search
None
See application file for complete search history.

(56) References Cited

U.S. PATENT DOCUMENTS 3,490,447 A * 1/1970 Jackson ............... A41D 13/11
128/863
4,136,222 A * 1/1979 Jonnes ............... B29D 24/005
428/116
(Continued)

FOREIGN PATENT DOCUMENTS

CN  2601698 Y * 2/2004 ............ A61M 16/06
CN  2741598 Y * 11/2005
(Continued)

OTHER PUBLICATIONS

Machine Translation of CN-2741598-Y, dated Nov. 2005 (Year: 2005).*
(Continued)

*Primary Examiner* — Jeffrey A Vonch
(74) *Attorney, Agent, or Firm* — Dority & Manning, P.A.

(57) ABSTRACT

A splash resistant multi-layered structure is provided. The structure includes a specific arrangement of layers of material and a plurality of three-dimensional spacers that helps prevent penetration through the structure by a fluid that contacts an outer surface of the structure due to a state of forced separation that exists between two adjacent layers of the structure due to the presence of the plurality of three-dimensional spacers positioned between the layers. The plurality of three-dimensional spacers can be positioned on one of the adjacent layers of the structure such that a
(Continued)

distance at least as large as the maximum height of the plurality of three-dimensional spacers separates the two layers from each other and can be present on a layer of material in a continuous or discontinuous pattern or can be present on a layer of material in a random fashion. The presence of the three-dimensional spacers can reduce the basis weight or eliminate one or more layers of the structure, which, in turn, can reduce thermal resistance, lower the pressure drop across the layers of the structure, and reduce the overall weight of the structure to enhance breathability and comfort.

19 Claims, 6 Drawing Sheets

(51) Int. Cl.

| | | |
|---|---|---|
| B32B 27/12 | (2006.01) | |
| B32B 27/18 | (2006.01) | |
| A41D 13/11 | (2006.01) | |
| A41D 13/12 | (2006.01) | |
| A41D 31/02 | (2019.01) | |
| A41D 31/102 | (2019.01) | |
| A61B 46/00 | (2016.01) | |
| A42B 1/04 | (2006.01) | |
| B32B 5/26 | (2006.01) | |
| B32B 5/32 | (2006.01) | |
| B32B 5/18 | (2006.01) | |
| B32B 3/08 | (2006.01) | |
| B32B 7/14 | (2006.01) | |
| B32B 3/22 | (2006.01) | |
| B32B 27/30 | (2006.01) | |
| B32B 27/06 | (2006.01) | |
| B32B 5/24 | (2006.01) | |
| B32B 27/32 | (2006.01) | |
| A41D 31/14 | (2019.01) | |
| A41D 31/30 | (2019.01) | |
| A41D 13/005 | (2006.01) | |
| A41D 31/28 | (2019.01) | |
| A62B 23/02 | (2006.01) | |
| F28D 20/02 | (2006.01) | |
| A62B 18/02 | (2006.01) | |
| A62B 17/00 | (2006.01) | |
| B32B 27/08 | (2006.01) | |

(52) U.S. Cl.
CPC .......... *A61B 46/40* (2016.02); *B32B 3/08* (2013.01); *B32B 3/22* (2013.01); *B32B 5/022* (2013.01); *B32B 5/18* (2013.01); *B32B 5/26* (2013.01); *B32B 5/32* (2013.01); *B32B 7/14* (2013.01); *B32B 27/12* (2013.01); *B32B 27/18* (2013.01); *B32B 27/308* (2013.01); *A41D 13/0053* (2013.01); *A41D 13/1192* (2013.01); *A41D 31/02* (2013.01); *A41D 31/102* (2019.02); *A41D 31/145* (2019.02); *A41D 31/285* (2019.02); *A41D 31/305* (2019.02); *A41D 2400/36* (2013.01); *A41D 2400/52* (2013.01); *A41D 2500/30* (2013.01); *A41D 2500/54* (2013.01); *A42B 1/043* (2013.01); *A62B 17/006* (2013.01); *A62B 18/02* (2013.01); *A62B 23/025* (2013.01); *B01D 2239/045* (2013.01); *B01D 2239/0407* (2013.01); *B01D 2239/0442* (2013.01); *B01D 2239/0478* (2013.01); *B01D 2239/0686* (2013.01); *B32B 5/245* (2013.01); *B32B 27/065* (2013.01); *B32B 27/08* (2013.01); *B32B 27/32* (2013.01); *B32B 2250/02* (2013.01); *B32B 2250/03* (2013.01); *B32B 2250/04* (2013.01); *B32B 2250/20* (2013.01); *B32B 2250/24* (2013.01); *B32B 2255/02* (2013.01); *B32B 2255/26* (2013.01); *B32B 2262/12* (2013.01); *B32B 2307/30* (2013.01); *B32B 2307/4023* (2013.01); *B32B 2307/56* (2013.01); *B32B 2307/70* (2013.01); *B32B 2307/718* (2013.01); *B32B 2307/724* (2013.01); *B32B 2307/7265* (2013.01); *B32B 2307/73* (2013.01); *F28D 20/023* (2013.01); *Y10T 428/24025* (2015.01); *Y10T 428/2457* (2015.01); *Y10T 428/24182* (2015.01); *Y10T 428/24562* (2015.01); *Y10T 428/24612* (2015.01); *Y10T 428/24826* (2015.01); *Y10T 428/24851* (2015.01); *Y10T 428/24893* (2015.01); *Y10T 428/254* (2015.01); *Y10T 442/659* (2015.04); *Y10T 442/66* (2015.04); *Y10T 442/68* (2015.04); *Y10T 442/681* (2015.04)

(56) References Cited

U.S. PATENT DOCUMENTS

| | | | | |
|---|---|---|---|---|
| 4,196,245 | A * | 4/1980 | Kitson | A41D 13/1209 428/198 |
| 4,510,193 | A * | 4/1985 | Blucher | C01B 32/336 428/196 |
| 4,555,811 | A * | 12/1985 | Shimalla | D04H 1/54 2/51 |
| 4,856,509 | A * | 8/1989 | Lemelson | A41D 13/1146 128/206.19 |
| 5,277,963 | A * | 1/1994 | von Blucher | A62B 23/00 428/196 |
| 5,294,258 | A * | 3/1994 | Jarrell | B05C 5/0254 118/410 |
| 5,366,801 | A * | 11/1994 | Bryant | D06N 3/0059 428/305.5 |
| 5,430,896 | A * | 7/1995 | Bisley | A41B 11/005 2/239 |
| 5,500,270 | A * | 3/1996 | Langdon | A61F 13/512 428/119 |
| 5,503,076 | A * | 4/1996 | Yeo | B32B 7/14 101/483 |
| 5,620,785 | A * | 4/1997 | Watt | A41D 13/11 128/206.12 |
| 5,656,167 | A * | 8/1997 | Martz | A41D 31/02 210/490 |
| 5,662,991 | A * | 9/1997 | Smolik | A61L 15/46 442/319 |
| 5,705,251 | A * | 1/1998 | Morman | A41D 13/1209 428/114 |
| 5,804,295 | A * | 9/1998 | Braun | A62B 23/02 428/323 |
| 5,860,163 | A * | 1/1999 | Aldridge | A41D 13/00 2/81 |
| 5,874,159 | A * | 2/1999 | Cruise | B32B 5/26 428/198 |
| 5,883,026 | A * | 3/1999 | Reader | A41D 13/11 128/206.12 |
| 5,913,406 | A * | 6/1999 | Lofgren | A41D 13/1209 2/51 |
| 6,080,418 | A * | 6/2000 | Sengupta | A01N 25/24 424/408 |
| 6,145,504 | A * | 11/2000 | Miyake | A41D 13/11 128/206.19 |
| 6,481,015 | B1 * | 11/2002 | Lanier | A41D 31/102 2/2.5 |
| 6,511,927 | B1 * | 1/2003 | Ellis | A41D 13/1209 442/77 |
| 6,638,605 | B1 * | 10/2003 | Ankuda, Jr. | A41D 13/1209 428/198 |

(56) References Cited

U.S. PATENT DOCUMENTS

| | | | |
|---|---|---|---|
| 6,942,894 B2* | 9/2005 | Alberg | B29C 43/222 156/291 |
| 8,091,550 B2 | 1/2012 | Steindorf | |
| 2002/0027101 A1* | 3/2002 | Insley | B01D 39/1692 210/488 |
| 2002/0034910 A1* | 3/2002 | Johnson | A43B 23/07 442/375 |
| 2002/0095711 A1* | 7/2002 | Saito | A41D 27/245 2/71 |
| 2002/0096051 A1* | 7/2002 | Kames | B60H 3/0658 96/154 |
| 2002/0193028 A1* | 12/2002 | Zuckerman | D06N 3/0061 442/328 |
| 2003/0040552 A1* | 2/2003 | Quong | A01N 31/02 523/208 |
| 2003/0054141 A1* | 3/2003 | Worley | D06N 3/0056 428/195.1 |
| 2004/0005832 A1* | 1/2004 | Neculescu | A61F 13/49017 442/149 |
| 2004/0033743 A1* | 2/2004 | Worley | D06M 23/02 442/59 |
| 2004/0043212 A1* | 3/2004 | Grynaeus | D04H 1/64 428/364 |
| 2004/0116025 A1* | 6/2004 | Gogins | B32B 7/14 442/340 |
| 2004/0219337 A1* | 11/2004 | Langley | B32B 5/26 428/198 |
| 2005/0079379 A1* | 4/2005 | Wadsworth | B32B 3/26 428/684 |
| 2005/0133036 A1* | 6/2005 | Steindorf | A41D 13/11 128/206.19 |
| 2005/0139217 A1* | 6/2005 | Chiam | A41D 13/11 128/206.19 |
| 2005/0150490 A1* | 7/2005 | Pears | A62D 5/00 128/200.24 |
| 2005/0191920 A1* | 9/2005 | Sadato | A41D 31/245 442/76 |
| 2005/0249917 A1* | 11/2005 | Trentacosta | G05D 22/02 428/137 |
| 2005/0252379 A1* | 11/2005 | Von Blucher | B01J 20/28011 96/154 |
| 2005/0266749 A1* | 12/2005 | De Ruiter | A41D 31/02 442/59 |
| 2006/0130842 A1* | 6/2006 | Kleman | A41D 13/11 128/206.19 |
| 2006/0174392 A1* | 8/2006 | Farnworth | A62B 17/005 2/102 |
| 2006/0188582 A1* | 8/2006 | Naylor Da Rocha Gomes | B01J 13/22 424/490 |
| 2007/0059504 A1* | 3/2007 | von Blucher | A62D 5/00 428/220 |
| 2007/0065658 A1* | 3/2007 | Bohringer | A62D 5/00 428/323 |
| 2008/0057809 A1* | 3/2008 | Rock | D06M 15/564 442/64 |
| 2008/0085210 A1* | 4/2008 | Griesbach | B01D 39/1623 422/21 |
| 2008/0195016 A1* | 8/2008 | Bottini | B32B 5/04 602/44 |
| 2008/0233368 A1* | 9/2008 | Hartmann | D06M 23/12 428/206 |
| 2009/0035557 A1* | 2/2009 | Hartmann | D02G 3/404 428/331 |
| 2009/0202936 A1* | 8/2009 | Morelissen | B41J 2/0057 430/124.32 |
| 2009/0211581 A1* | 8/2009 | Bansal | B32B 3/28 128/206.19 |
| 2009/0320177 A1* | 12/2009 | Lin | A41D 13/1209 2/114 |
| 2010/0186435 A1* | 7/2010 | Vogel | A41D 13/0053 62/259.3 |
| 2010/0212071 A1* | 8/2010 | Bohringer | B01J 20/20 2/400 |
| 2010/0300054 A1* | 12/2010 | Cole | A62D 5/00 55/524 |
| 2010/0313759 A1* | 12/2010 | Bones | B01J 20/20 96/12 |
| 2012/0015155 A1* | 1/2012 | Blackford | A43B 23/0235 428/189 |
| 2012/0160246 A1* | 6/2012 | Nguyen | A62B 23/025 128/206.19 |
| 2012/0160247 A1* | 6/2012 | Quincy, III | A41D 13/11 128/206.19 |
| 2012/0244312 A1* | 9/2012 | Pearce | D06N 7/0092 428/136 |
| 2013/0133353 A1* | 5/2013 | Araujo | B29C 69/00 62/331 |
| 2013/0146061 A1* | 6/2013 | Tushaus | B29C 70/12 128/206.12 |
| 2013/0291877 A1* | 11/2013 | Nguyen | A62B 23/025 128/863 |
| 2014/0053311 A1* | 2/2014 | Nordstrom | B32B 5/022 2/69 |
| 2014/0069624 A1* | 3/2014 | Blackwell | D21H 13/24 165/185 |
| 2014/0220328 A1* | 8/2014 | Ausen | B29C 48/3363 428/219 |
| 2014/0228796 A1* | 8/2014 | Burvall | A61F 13/494 604/385.01 |
| 2014/0234606 A1* | 8/2014 | Ausen | B29C 48/345 428/220 |
| 2014/0255664 A1* | 9/2014 | Gartmann | D06M 15/19 428/196 |
| 2015/0013681 A1* | 1/2015 | Stockhamer | A41B 15/00 128/206.14 |
| 2015/0106992 A1* | 4/2015 | Blakely | A41D 13/0056 2/69 |
| 2015/0147539 A1 | 5/2015 | Thomas et al. | |
| 2015/0210032 A1* | 7/2015 | Blackford | D06N 7/0092 428/196 |
| 2015/0223533 A1* | 8/2015 | Blakely | A41D 31/06 428/196 |
| 2015/0238783 A1* | 8/2015 | Nguyen | A62B 18/02 128/205.27 |
| 2015/0296994 A1* | 10/2015 | Mikkelsen | A47C 21/046 5/655.4 |
| 2016/0001101 A1* | 1/2016 | Sabolis | A62B 9/02 128/863 |
| 2016/0114280 A1* | 4/2016 | Dunaway | B01D 46/10 128/863 |
| 2016/0183610 A1* | 6/2016 | Ying | A41D 13/11 128/863 |
| 2017/0071268 A1* | 3/2017 | Pan | A41D 27/28 |
| 2017/0071275 A1* | 3/2017 | Darby | A41D 31/14 |
| 2017/0113200 A1* | 4/2017 | Zhang | A61Q 17/04 |
| 2017/0172218 A1* | 6/2017 | Khan | A61F 13/8405 |
| 2017/0273377 A1* | 9/2017 | Aihara | A41B 1/08 |
| 2017/0274228 A1* | 9/2017 | Nguyen | A62B 18/084 |
| 2018/0215130 A1* | 8/2018 | Hottner | B32B 27/322 |
| 2018/0271184 A1* | 9/2018 | Shalev | A41D 13/0053 |
| 2018/0305860 A1* | 10/2018 | Mondal | D06M 15/53 |
| 2018/0313029 A1* | 11/2018 | Terras | D06M 13/02 |
| 2019/0069611 A1* | 3/2019 | Potnis | A41D 13/0053 |
| 2019/0110529 A1* | 4/2019 | Yamada | A41D 3/04 |

FOREIGN PATENT DOCUMENTS

| | | | | |
|---|---|---|---|---|
| CN | 101392461 | A | * 3/2009 | A62B 17/001 |
| CN | 201833634 | U | * 5/2011 | |
| CN | 102960874 | A | * 3/2013 | |
| CN | 202781979 | U | * 3/2013 | |
| CN | 205167704 | U | * 4/2016 | |
| DE | 29815881 | U1 | 1/2000 | |
| DE | 19850997 | A1 | * 5/2000 | A62D 5/00 |
| DE | 102006026788 | A1 | * 12/2007 | |
| DE | 102007062372 | A1 | * 6/2009 | A61L 31/16 |
| EP | 0353972 | A1 | * 2/1990 | A61F 13/025 |
| EP | 0818230 | A1 | * 1/1998 | B01D 39/00 |

(56) References Cited

FOREIGN PATENT DOCUMENTS

| FR | 1213415 A | * | 3/1960 | ........... A62B 17/001 |
|----|-----------|---|--------|-------------------------|
| FR | 2846202 A1 | * | 4/2004 | ........... A41D 31/085 |
| GB | 2077141 A | * | 12/1981 | ................ B32B 5/30 |
| GB | 2095616 A | * | 10/1982 | ................ B32B 5/26 |
| GB | 2 409 649 A | | 7/2005 | |
| IT | 20110638 A1 | * | 5/2013 | |
| JP | 2007037737 A | * | 2/2007 | |
| JP | 2014217461 A | * | 11/2014 | ................ B32B 5/02 |
| KR | 100660605 B1 | * | 12/2006 | ............. A61L 31/16 |
| WO | WO-9935926 A1 | * | 7/1999 | ........... A41D 31/085 |
| WO | WO-2004110541 A1 | * | 12/2004 | ........... A61M 16/06 |
| WO | WO-2012136962 A1 | * | 10/2012 | ................ B32B 5/02 |
| WO | WO-2017117432 A1 | * | 7/2017 | ............. B32B 15/14 |

OTHER PUBLICATIONS

International Search Report & Written Opinion for PCT/US2017/026908, dated Jul. 14, 2017, 11 pages.

\* cited by examiner

MULTI-LAYERED STRUCTURE AND ARTICLES FORMED THEREFROM HAVING IMPROVED SPLASH RESISTANCE BY INCREASED INTERLAYER SPACING

RELATED APPLICATION

The present application is the national stage entry of International Patent Application No. PCT/US2017/026908 having a filing date of Apr. 11, 2017, which claims priority to U.S. Provisional Application Ser. No. 62/325,712, filed on Apr. 21, 2016, both of which are incorporated herein in their entirety by reference thereto.

BACKGROUND OF THE INVENTION

The use of face masks and other personal protective equipment (PPE) such as surgical gowns, surgical drapes, bouffant caps, etc. is a recommended practice in the healthcare industry to help prevent the spread of disease. For instance, face masks worn by healthcare providers help reduce infections in patients by filtering the air exhaled from the wearer thus reducing the number of harmful organisms or other contaminants released into the environment.

This is especially important during surgeries where the patient is much more susceptible to infection due to the presence of an open wound site. Similarly, patients with respiratory infections may use face masks to prevent the spread of disease by filtering and containing any expelled germs. Additionally, face masks protect the healthcare worker by filtering airborne contaminants and microorganisms from the inhaled air.

Some diseases, such as hepatitis and AIDS, can be spread through contact of infected blood or other body fluids to another person's mucous membranes (i.e., eyes, nose, mouth, etc.). The healthcare industry recommends specific practices to reduce the likelihood of contact with contaminated body fluids. One such practice is to use face masks, surgical gowns, surgical drapes, bouffant caps, and other similar PPE, which are resistant to penetration from a splash of body fluids.

The material used to form such PPE can be comprised of several layers. The layer that is positioned closest to the skin of the wearer is typically referred to as the inner layer. The layer furthest from the skin of the wearer is referred to as the outer layer. An additional layer or layers of material can be disposed between the outer layer and the inner layer. Typically, one of these additional layers is a filtration layer, such as a microfiber fiberglass layer or an electret-treated meltblown layer.

As stated, face masks, surgical gowns, surgical drapes, bouffant caps, and other similar PPE may be designed to be resistant to penetration by splashes of fluids so that pathogens found in blood or other fluids are not able to be transferred to skin of the user of such PPE. The American Society of Testing and Materials (ASTM) has developed test method F1862-13, *"Standard Test Method of Resistance of Medical Face Masks to Penetration by Synthetic Blood (Horizontal Projection of Fixed Volume at a Known Velocity"* (2013) to assess an article's ability to resist penetration by a splash at three levels of pressure. This method is referenced in ASTM F2100-11, *"Standard Specification for Performance of Materials Used in Medical Face Masks"* (2011), which specifies a set of performance criteria for medical face masks. To achieve Level 3 performance, which is the most stringent level of testing in ASTM F2100-11, a face mask must resist splashes of 2 milliliters of synthetic blood (available from Johnson, Moen & Co., 2505 Northridge Lane NE, Rochester, Minn. 55906) at 160 mmHg per the ASTM F1862-13 procedure.

The splash resistance of an article of PPE (e.g., a face mask, etc.) is typically a function of the ability of the layer or layers of the structure used in the article to resist fluid penetration, and/or their ability to reduce the transfer of the energy of the fluid splash to subsequent layers, and/or their ability to absorb the energy of the splash. Typical approaches to improving splash resistance are to use thicker materials or additional layers in the construction of the structure. However, these solutions may increase the cost of the structure, increase the weight of the structure, reduce the porosity of the structure, and add discomfort to the wearer by negatively impacting the thermal resistance of the multi-layered structure.

An additional approach to improving the splash resistance of materials or structures used to form face masks, surgical gowns, surgical drapes, bouffant caps, or other similar PPE is to incorporate a layer of porous, high loft, fibrous material. This type of material is advantageous in that the layer will absorb or dissipate the energy of the impact of the fluid splash. However, it is often the case that fluid will saturate this high loft material, hence reducing its effectiveness in absorbing the energy of a future fluid splash. Additionally, fluid can be squeezed out of this high loft material and may be transferred through subsequent layers upon compression of the multi-layered structure.

As such, a need exists for a structure and articles formed therefrom having improved splash resistance but without imparting discomfort to the user.

SUMMARY OF THE INVENTION

According to one embodiment, the present invention provides for a splash resistant multi-layered structure. The multi-layered structure includes an outer layer of material having an outer-facing surface and an inner-facing surface; an inner layer of material having an outer-facing surface and an inner-facing surface; and a first plurality of three-dimensional spacers disposed on a surface within the multi-layered structure. The plurality of three-dimensional spacers define a space between the outer layer of material and the inner layer of material, where the space spans a distance at least as great as a maximum height of the plurality of three-dimensional spacers, and the plurality of three-dimensional spacers aid in absorbing energy associated with a fluid contacting the outer layer of material.

In one particular embodiment, the first plurality of three-dimensional spacers define a first plurality of channels for redirecting the flow of fluid that strikes the outer layer of material, where the channels have an orientation such that the fluid is directed laterally away from the point of contact of the fluid through the channels.

In another embodiment, the first plurality of three-dimensional spacers are arranged in a pattern. The pattern can be continuous or discontinuous. For instance, the pattern can include a plurality of dots, where the dots are arranged on a layer of material in a series of columns and a series of rows.

In still another embodiment, the first plurality of three-dimensional spacers comprises a binder, an ink, an adhesive, or a combination thereof. For instance, the first plurality of three-dimensional spacers can include an acrylic binder or an elastic or non-elastic expandable ink. Further, the first plurality of three-dimensional spacers can include an encapsulated functional additive contained within the binder, the ink, the adhesive, of the combination thereof, where the functional additive can be a phase change material, a fragrance, an absorbent material, a superabsorbent material, an antimicrobial, a therapeutic agent, a topical ointment, or a combination thereof. Moreover, the functional additive can be present in an amount ranging from about 0.25 wt. % to about 70 wt. % based on the dry weight of the first plurality of three-dimensional spacers present within the multi-layered structure.

In yet another embodiment, the multi-layered structure can include an additional layer of material disposed between the outer layer of material and the inner layer of material.

Further, the first plurality of three-dimensional spacers can be disposed on an outer-facing surface of the additional layer of material. Moreover, the additional layer of material can be a spunbond web positioned adjacent the outer layer of material, where the structure can further include a meltblown web, where the meltblown web can be positioned adjacent the inner layer of material.

In one more embodiment, the multi-layered structure can include a second plurality of three-dimensional spacers, where the second plurality of three-dimensional spacers are disposed on an inner-facing surface of the inner layer of material, and where the first plurality of three-dimensional spacers can include an acrylic binder and the second plurality of three-dimensional spacers can include a phase change material encapsulated within an acrylic binder.

In still another embodiment, the additional layer of a material is a meltblown web. When the additional layer of material is a meltblown web, the first plurality of three-dimensional spacers can be disposed on the inner-facing surface of the outer layer of material or the first plurality of three-dimensional spacers can be disposed on an inner-facing surface of the meltblown web.

In either scenario, the multi-layered structure can include a second plurality of three-dimensional spacers, where the second plurality of three-dimensional spacers can disposed on an inner-facing surface of the inner layer of material, the first plurality of three-dimensional spacers can include an acrylic binder, and the second plurality of three-dimensional spacers can include a phase change material encapsulated within an acrylic binder.

In one more embodiment, the outer layer of material and the inner layer of material can each include a spunbond web.

In an additional embodiment, the present invention contemplates an article such as a face mask, a surgical gown, a surgical drape, a surgical protective hood/headwear, or a bouffant cap formed from the multi-layered structure described above.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
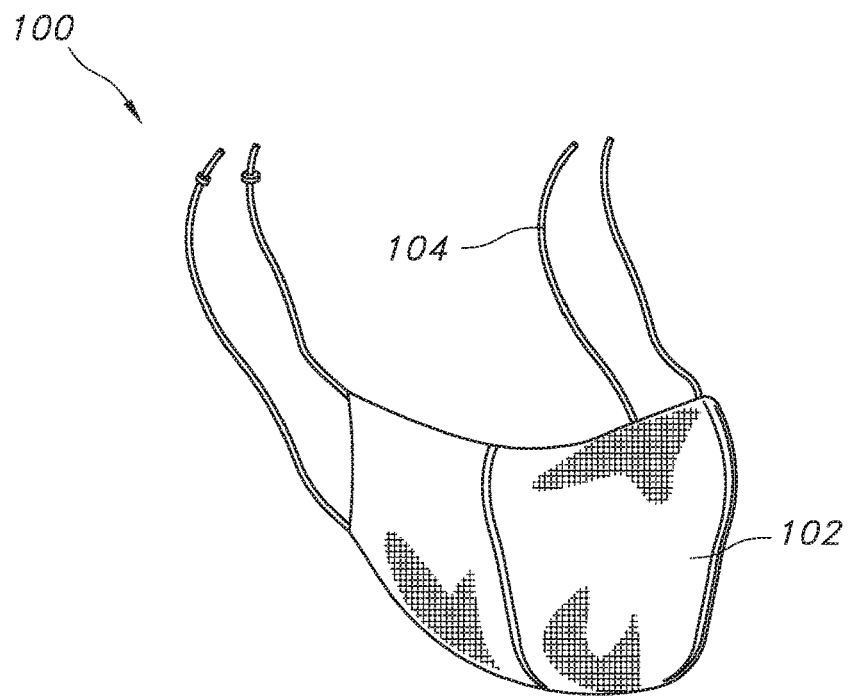
FIG. 1 is a perspective view of a face mask having a body portion that can be formed from a multi-layered structure contemplated by the present invention.

Repeat use of reference characters in the present specification and drawings is intended to represent the same or analogous features or elements of the present invention.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features will be represented by like numbers between the figures.

Generally speaking, the present invention is directed to a splash resistant multi-layered structure. The splash resistance of the multi-layered structure is facilitated by a state of forced separation between adjacent layers of the multi-layered structure, such as between an inner-facing surface (i.e., a layer that faces towards the skin of a user) of a first layer of material and an outer-facing surface (i.e., a layer that faces away from the skin of a user) of a second layer of material. The forced separation between the two adjacent layers of material is the result of the presence of a plurality of three-dimensional spacers positioned between the adjacent layers of the multi-layered structure, where the plurality of three-dimensional spacers can be positioned on one or both of the adjacent layers of the multi-layered structure such that a distance at least as large as the maximum height of the plurality of three-dimensional spacers separates the two layers from each other. The three-dimensional spacers can be present on a layer of material in a continuous or discontinuous pattern or can be present on a layer of material in a random fashion. As a result of the plurality of three-dimensional spacers present between two layers of the multi-layered structure, a plurality of channels can be formed between the layers to increase the interlayer spacing so that the splash resistance and fluid barrier capabilities of the multi-layered structure can be enhanced by facilitating the lateral spread of fluid once the fluid contacts the multi-layered structure. Further, the stiffness provided by the three-dimensional spacers can facilitate the lateral dissipation of energy to prevent compression of the layers of the multi-layered structure when a fluid insult occurs. Such an arrangement prevents fluid from penetrating through the entire multi-layered structure, which could endanger the health of the user when the multi-layered structure is formed into PPE. Moreover, the presence of the three-dimensional spacers can reduce the number of layers of material required to form a multi-layered structure having sufficient splash resistance. Likewise, the presence of the three-dimensional spacers can enable the use of materials with lower basis weights to form a PPE article, which can increase the comfort of the user. Specifically, the reduction in basis weight or elimination of one or more layers of material can reduce thermal resistance, lower the pressure drop across the layers of the multi-layered structure, and reduce the overall weight of the multi-layered structure to enhance breathability and comfort.

Alternatively and/or additionally, it is contemplated that the filter material component or filtration layer of the multi-layered structure may be modified to take advantage of the splash resistance and fluid barrier capabilities of the multi-layered structure. Meltblown fabrics (and/or other filtration media) used in conventional multi-layered structures for articles such as face masks are selected to provide greater resistance to penetration by liquids as part of the multi-layered structure. As a result, the meltblown fabrics (and/or other filtration media) may have unnecessarily high basis weights and/or unnecessarily high levels of pressure drop. According to an aspect of the present invention, the advantageous splash resistance and fluid barrier capabilities of the multi-layered structure enable use of meltblown fabrics (and/or other filtration media) having lower basis weights and/or lower levels of pressure drop. Moreover, the greater "breathability" of the meltblown fabrics (and/or other filtration media) provides more efficient energy transfer between phase change material and air exchanged during a respiration cycle. This is believed to be significant at least because it allows for the economical and efficient use of phase change material in an article such as a face mask. As a result, less phase change material may be needed to accomplish a threshold level of energy transfer, which important because it reduces the amount of an expensive component in a disposable article and can have a very large impact on the commercial viability of such disposable articles. The modification is also significant because it enables the manufacture of practical and economical face masks having a smaller face mask area while maintaining or even increasing filtration efficiency, protection, and/or user comfort. As a result of using less or fewer materials and/or decreasing mask size, one can reduce the cost of a disposable article which can have a very large impact on the commercial viability of such disposable articles.

Figure 2:
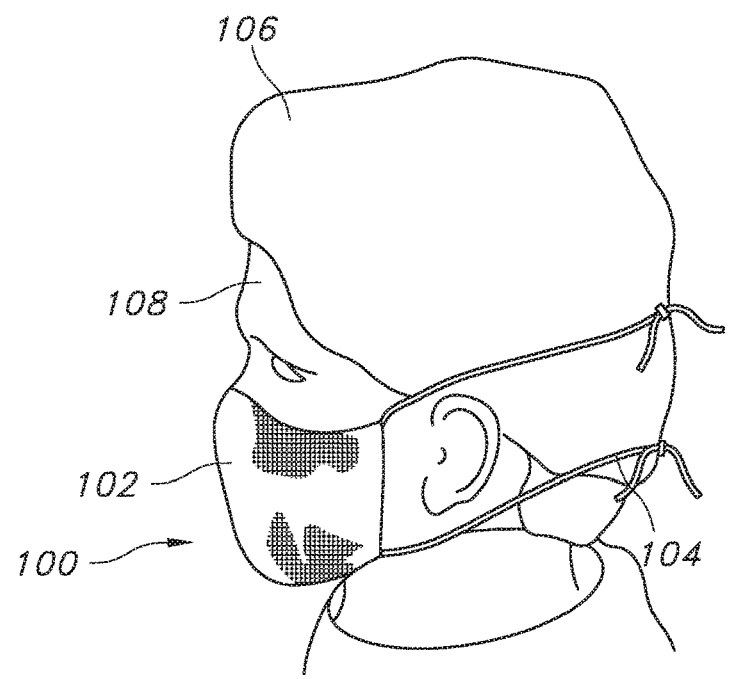
FIG. 2 is a perspective view of a face mask with a body portion where the face mask is attached to the head of a user.

FIGS. 1 and 2 show a face mask 100 which may be formed from the multi-layered splash resistant structure contemplated by the present invention. The face mask 100 includes a body portion 102 that is configured to be placed over the mouth and at least part of the nose of the user 108 such that the air exchanged through normal respiration passes through the body portion 102 of the face mask 100. It is to be understood, however, that the body portion 102 can be of a variety of styles and geometries, such as, but not limited to, flat half mask, pleated face masks, cone masks, flat folded personal respiratory devices, duckbill style mask, trapezoidally shaped masks, etc. The body portion 102 may be configured to have one or more horizontal pleats, one or more vertical pleats, or no pleats, where such designs are generally known in the art. The face mask 100 therefore isolates the mouth and the nose of the user 108 from the environment. The face mask 100 is attached to the user 108 by a pair of tie straps 104 which are wrapped around the head of the user 108 (and a hair cap 106 if worn by the user) and are connected to one another. It is to be understood, however, that other types of fastening arrangements may be employed in accordance with various exemplary embodiments of the present invention. For instance, instead of the tie straps 104, the face mask 100 may be attached to the user 108 by ear loops, elastic bands wrapping around the head, or a hook and loop type fastener arrangement, or the face mask 100 may be wrapped as a single piece around the head of the user 108 by an elastic band. The face mask 100 may also be directly attached to the hair cap 106.

Additionally, the configuration of the face mask 100 may be different in accordance with various exemplary embodiments. In this regard, the face mask 100 may be made such that it covers both the eyes, hair, nose, throat, and mouth of the user. As such, the present invention is not limited to only face masks 100 that cover only the nose and mouth of the user 108.

Figure 3:
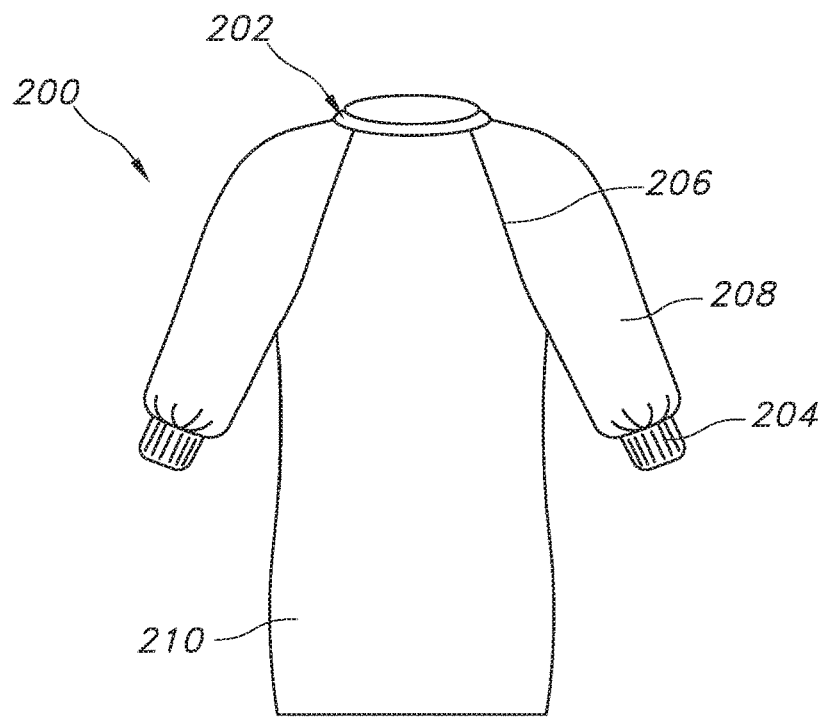
FIG. 3 is a front view of a surgical gown that can be formed from the multi-layered structure contemplated by the present invention.

Meanwhile, FIG. 3 shows a front view of a surgical gown 200 that can be formed from the splash resistant multi-layered structure contemplated by the present invention. The gown 200 can include a collar 202, cuffs 204, and shoulder seams 206 that link the sleeves 208 to the main body 210. Other exemplary articles that can be formed from the splash resistant multi-layered structure of the present invention include surgical drapes or any other PPE in which splash resistant characteristics are desired. Further, the multiple layers of material in the multi-layered structure used to form the aforementioned face masks, surgical gowns, drapes, surgical protective hoods/headwear, bouffant caps, etc. contemplated by the present invention may be joined by various methods, including adhesive bonding, thermal point bonding, or ultrasonic bonding.

The various components of the multi-layered splash resistant structure of the present invention are discussed in more detail below.

I. Plurality of Three-Dimensional Spacers

The multi-layered splash resistant structure of the present invention includes a plurality of three-dimensional spacers that are disposed on one or more outer-facing surfaces (i.e., surfaces facing away from the skin of the user) or inner-facing surfaces (i.e., surfaces facing towards the skin of the user) of the multi-layered structure. The plurality of three-dimensional spacers can be formed from a composition that includes a binder, an ink, a polymer, or a combination thereof, or any other component that can form a three-dimensional spacer when applied to one of the layers of material used to form the multi-layered structure, where such layers of material are discussed in more detail below. Specific examples of binders that can be suitable for forming the three-dimensional spacers contemplated by the present invention include an elastic puff (expandable) printing ink, a non-elastic puff (expandable) printing ink, an acrylic binder, a polyurethane binders, a thermoplastic material (e.g., a low temperature polyolefin hot melt adhesive or glue; a printing ink, or any other suitable binder, ink, adhesive, etc. or a combination thereof. Such binders can be obtained from Lubrizol or H. B. Fuller. Further, the binders can be water soluble. Although not required, in one embodiment, such binders, inks, adhesives, etc. can be hydrophobic, where the hydrophobicity of the binder, ink, adhesive, etc. can the enhance splash resistance by preventing fluid from penetrating subsequent layers of the article.

In one particular embodiment, the three-dimensional spacers can be formed from heat-activatable expandable inks, such as AQUAPUFF™ inks obtainable from Polytex Environmental Inks (Bronx, N.Y.). Other commercially available inks are available from Eastern Color and Chemical Company (Greenville, S.C.), International Coatings Company (Cerritos, Calif.), Dongguan City Haiya Printing Material Company (China), Atlas Screen Supply Company (Schiller Park, Ill.), NEHOC Australia Pty, Limited (Australia), and INX International Ink Corporation (Schaumburg, Ill.). Such inks are expandable inks which react when exposed to heat to produce a reaction that causes the ink to expand or "puff" into a three-dimensional structure. The inks may include additives, known in the art as blowing agents, and can include chemicals which undergo physical or chemical changes on heating to form a gaseous product. Such additives include EXPANCEL™ 461 DU Microsphere (supplied by Expancel), Unicell OH (supplied by OMYA), Genitron LE (supplied by Acrol), or other gas-encapsulated thermoplastic microspheres. The printing of such inks onto one or more layers of the multi-layered structure of the present invention can occur at a number of steps in the process, such as in an off-line printing step, or on-line during the article assembly process. Further, the ink can be printed at one process step, and expanded by heat activation in a later, downstream step.

In some embodiments, the three-dimensional spacers can include an optional amount of moisture absorbing polymer. The polymer can be present in the three-dimensional structures spacers in an amount as desired. For example, in some aspects, the three-dimensional spacers can contain up to about 1 wt. %, such as up to about 5 wt. %, or even up to about 10 wt. % or more of a moisture absorbing polymer. Examples of suitable moisture absorbing polymers include, but are not limited to, polyethylene oxide, polyethylene glycol, polyvinyl alcohol, polyvinyl pyrrolidones, polyvinyl pyridine, or a combination thereof.

In some embodiments, the three-dimensional spacers can include an optional elastomeric polymer. The elastomeric polymer can make the foam structure resilient and can help with moisture absorbency by trapping water like a sponge. Further, the elastomeric polymer may add resilience or flexibility to the three-dimensional spacers. The elastomeric polymer component can be present in an amount which is effective to achieve the desired dimensional change properties. For example, the three-dimensional spacers can contain up to about 1 wt. %, such as up to about 5 wt. %, or even up to about 10 wt. % or more of an elastomeric polymer to provide improved properties. Examples of suitable elastomeric polymers include, but are not limited to, thermoplastic polyurethanes, olefinic elastomeric polymers (Vistamaxx®), poly(ether-amide) block copolymers, thermoplastic rubbers such as uncrosslinked polyolefins, styrene-butadiene copolymers, silicon rubbers, synthetic rubbers such as nitrile rubber, styrene isoprene copolymers, styrene ethylene butylenes copolymers, butyl rubber, nylon copolymers, spandex fibers comprising segmented polyurethane, ethylene-vinyl acetate copolymer or a combination thereof.

Additionally, adhesion promoters can be added to the three-dimensional spacers. For example, Carboset 514H, available commercially from Noveon, Inc. of Cleveland, Ohio, is an acrylic colloidal dispersion polymer supplied in ammonia water, which can dry to a clear, water-resistant, non-tacky thermoplastic film. Such adhesion promotes facilitate the attachment of the three-dimensional spacers to the layer of material on which they are applied.

In addition, the three-dimensional spacers can contain a coloring agent (e.g., pigment or dye), a solvent, and any other desired ingredients. Typically, a pigment refers to a colorant based on inorganic or organic particles which do not dissolve in water or solvents. Usually pigments form an emulsion or a suspension in water. On the other hand, a dye generally refers to a colorant that is soluble in water or solvents. The pigment or dye can be present in the three-dimensional spacers in an amount ranging from about 0.25 wt. % to about 40 wt. %, such as from about 0.5 wt. % to about 30 wt. %, such as from about 1 wt. % to about 20 wt. % on a dry weight basis after the spacers have formed to the layer of material on which they have been applied.

Suitable organic pigments include dairylide yellow AAOT (for example, Pigment Yellow 14 CI No. 21 095), dairylide yellow AAOA (for example, Pigment Yellow 12 CI No. 21090), Hansa Yellow, CI Pigment Yellow 74, Phthalocyanine Blue (for example, Pigment Blue 15), lithol red (for example, Pigment Red 52:1 CI No. 15860:1), toluidine red (for example, Pigment Red 22 CI No. 12315), dioxazine violet (for example, Pigment Violet 23 CI No. 51319), phthalocyanine green (for example, Pigment Green 7 CI No. 74260), phthalocyanine blue (for example, Pigment Blue 15 CI No. 74160), naphthoic acid red (for example, Pigment Red 48:2 CI No. 15865:2). Suitable inorganic pigments include titanium dioxide (for example, Pigment White 6 CI No. 77891), carbon black (for example, Pigment Black 7 CI No. 77266), iron oxides (for example, red, yellow, and brown), ferric oxide black (for example, Pigment Black 11 CI No. 77499), chromium oxide (for example, green), ferric ammonium ferrocyanide (for example, blue), and the like.

Suitable dyes that may be used include, for instance, acid dyes, and sulfonated dyes including direct dyes. Other suitable dyes include azo dyes (e.g., Solvent Yellow 14, Dispersed Yellow 23, and Metanil Yellow), anthraquinone dyes (e.g., Solvent Red 111, Dispersed Violet 1, Solvent Blue 56, and Solvent Orange 3), xanthene dyes (e.g., Solvent Green 4, Acid Red 52, Basic Red 1, and Solvent Orange 63), azine dyes (e.g., Jet Black), and the like.

The three-dimensional spacers can be applied to an outer-facing surface or an inner-facing surface of any layer of material present in the multi-layered splash resistant structure of the present invention. To apply the spacers, the ink, binder, or polymer composition is generally dispersed or dissolved in water or another low viscosity carrier. In addition to using water as a solvent, exemplary solvents that can be used may include aliphatic hydrocarbons with common binder types, such as polyamide, shellac, nitro-cellulose, and styrene-maleic. Generally, solvent-based treatments include non-catalytic, block urethane resin, which generally demonstrate superior durability over traditional flexographic binders, such as styrene-maleic, rosin-maleic, and acrylic solutions. Desired solvent blends include various acetates such as ethyl acetate, N-propyl acetate, isopropyl acetate, isobutyl acetate, N-butyl acetate, and blends thereof; various alcohols including ethyl alcohol, isopropyl alcohol, normal propyl alcohol, and blends thereof; and glycol ethers including EKTASOLVE™, EP (ethylene glycol monopropyl ether), EB (ethylene glycol monobutyl ether), DM (diethylene glycol monomethyl ether), DP (diethylene glycol monopropyl ether), and PM (propylene glycol monomethyl ether), which may be obtained from Eastman Chemical of Kingsport, Tenn. Other glycols that may also be used are DOWANOL™ obtainable from Dow Chemical of Midland, Mich. A desired solvent blend may be a blend of about 50% to about 75% glycol ether, about 25% to about 35% N-propyl acetate, and about 15% to about 25% N-butyl acetate.

Suitable water-based three-dimensional spacers that may be used may further include emulsions that may be stabilized in water-ammonia and may further comprise alcohols, glycols, or glycol ethers as co-solvents. Generally, organic solvents (less than or equal to about 7 wt. %) may be added to water-based treatments: alcohols, for example, propan-2-ol may be added for speeding up drying and assisting wetting, glycols, for example, mono propylene glycol to slow down drying, glycol ethers, for example, dipropyl glycol mono methyl ether to aid film formation. Such solvents may be commodity chemicals, commercially available from various companies. Generally, water-based treatments include self-crosslinking acrylic copolymer emulsion, which may have demonstrated superior durability over traditional non-crosslinking binders such as acrylic solutions and dispersion copolymers. Besides the solvent and pigments, the heat-activatable expandable treatment may comprise a binder. The binder helps stabilize the composition used to form the three-dimensional spacers onto the layer of material to which it is being applied.

In addition, one or more encapsulated functional additives can be combined within one of the binders, adhesives, or inks discussed above and then applied to one or more layers of the multi-layered structure of the present invention to provide an added benefit to the user of the multi-layered structure. The functional additive can be released from its encapsulant upon crushing of the microencapsulated functional additive, which could occur when the article of the present invention is opened from its packaging, unfolded, etc. or when the article of the present invention is wetted with a fluid. For instance, the plurality of three-dimensional spacers can include a phase change material (PCM) to provide for cooling, an antimicrobial agent to provide antimicrobial protection, a fragrance for odor control, a topical ointment for skincare, a therapeutic agent to provide a specific treatment, an absorbent material such as activated carbon for moisture or odor control, a superabsorbent material, or any other additive that could be useful in an article used as PPE. For instance, a fragrance can be encapsulated into microcapsules that are then incorporated into a binder to form the three-dimensional spacers of the present invention, and when an article containing the three-dimensional spacers is wetted, the fragrance could be released due to "crushing" or "disintegration" of the microcapsules containing the fragrance in order to mask an odor or release a scent, perhaps as an indicator of the article or layer of material being splashed. In another embodiment, a superabsorbent material can be incorporated into a binder to form the three-dimensional spacers of the present invention, and when an article containing the three-dimensional spacers is wetted, the superabsorbent material could be activated in order to help contain the a fluid insult. It should be understood that although "crushing" or "disintegration" of the microcapsules containing the antimicrobial, fragrance, topical ointment, or therapeutic agent may be required to activate such additives, "crushing" or "disintegration" of the microcapsules containing the phase change material functional additive, the absorbent material, or the superabsorbent material is not required.

Regardless of the particular encapsulated functional additives utilized, the functional additives can be encapsulated in such a way to provide functional permanency over longer time or to provide time-release of the functionalities mentioned above over different frequencies of time. Such additives can be present in the three-dimensional spacers in an amount ranging from about 0.25 wt. % to about 70 wt. %, such as from about 0.5 wt. % to about 60 wt. %, such as from about 1 wt. % to about 50 wt. % on a dry weight basis after the spacers have formed to the layer of material on which they have been applied.

Figure 4:
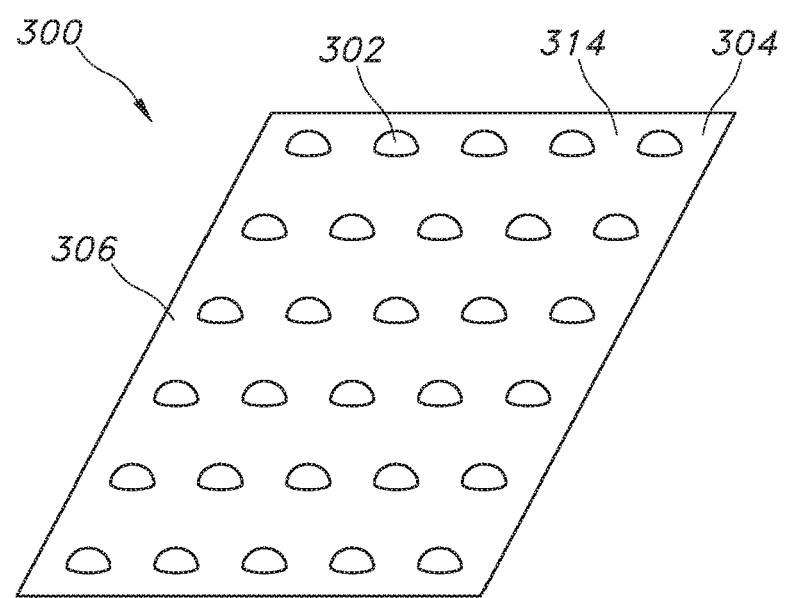
FIG. 4 is a perspective view of a layer of material that can be used in the multi-layered structure of the present invention, where a plurality of three-dimensional spacers has been applied to a surface of the material.

Moreover, the specific composition of the plurality of three-dimensional spacers, the three-dimensional spacers can be applied to one or more layers of material of the multi-layered structure of the present invention in any suitable pattern or in a random fashion. If the three-dimensional spacers are applied in a pattern, the pattern can be continuous or discontinuous. In one particular embodiment as shown in FIG. 4, the three-dimensional spacers 302 can be applied to a layer of the multi-layered structure 300 in the form of a series dots having a semi-circular shape and a maximum height S, where the dots are arranged in a series of offset columns 304 and a series of offset rows 306 to form channels 314 therebetween. In other embodiments, the three-dimensional spacers can be in the form of lines, crosses, gridlines, logos, or any other form or shape and can have any density, height, or texture so long as the three-dimensional spacers provide for sufficient spacing between the layers of material used to form the multi-layered structure of the present invention so that the splash resistant properties of the multi-layered structure can be achieved. In any event, the particular dimensions, shape, and spacing of the three-dimensional spacers is a function of the materials being used. As the intent is to provide a gap between the layers of materials used to form an article in order to dissipate the energy of the impact of the splash, the stiffer the layers are, especially the outer layer, the smaller, shorter, and more disperse the three-dimensional spacers (e.g., dots) can be. Meanwhile, as the drapability or flexibility of the outer layer of material increases, the three-dimensional spacers (e.g., dots) may need to be taller and/or closer together in order to minimize the potential contact between the adjacent layers of material, where such contact is what leads to fluid transfer through the subsequent layer.

Once applied to a layer of material, the three-dimensional spacers can have various textures. For instance, as discussed above, the three-dimensional spacers can be "puffy" or malleable (e.g., soft and cushiony), which can impart improved pressure distribution capabilities to the multi-layered structure incorporating the three-dimensional spacers, such as when the multi-layered structure is used in a face mask, or the three-dimensional spacers can have a rigid texture to provide the multi-layered structure with structural stability and prevent compression of the multi-layered structure when a fluid insult occurs. It should also be understood that the three-dimensional spacers can be present on from about 5% to about 100%, such as from about 10% to about 99.5%, such as from about 15% to about 99% of the surface area of the layer of material on which the three-dimensional spacers are applied. Further, the three-dimensional spacers can be applied to a layer of material in a composition that also includes a binder or carrier using any known method such as a gravure roll, slot coating, continuous spraying, discontinuous spraying, screen printing, ink jet printing, etc. In addition, heat can be applied after a composition containing the three-dimensional spacers has been applied to a layer of material to activate the plurality of three-dimensional characteristics of the spacers present on the layer of material, such as when the three-dimensional spacers are in the form of a "puffable" ink.

Regardless of the particular type of material used to form the three-dimensional spacers, the three-dimensional spacers can be in the form of dots, grids, logos, crosses, etc. which can have a width, length, or diameter of from about 0.25 mm to about 5 mm and can have a height S ranging from about 0.025 mm to about 3 mm. Further, the three-dimensional spacers can be hard, soft, or foam-like as needed by the application. In addition, the three-dimensional spacers (e.g., dots, crosses, logos, etc.) can be applied to the various layers of the multi-layered structure in an amount ranging from about 1% to about 70% of the total surface area of the surface to which the spacers are applied for breathable barrier or porous materials and in an amount ranging from about 1% to about 100% of the total surface area of the surface to which the spacers are applied for non-porous/non-breathable materials.

II. Layers of Material

The plurality of three-dimensional spacers discussed above can be applied to one or more layers of material in the multi-layered structure contemplated by the present invention. For example, the layers of the multi-layered structure can be formed from one or more non-woven materials (e.g., a spunbond, meltblown, SMS laminate, spunlace, hydroentangled, carded, elastomeric, or foam webs), one or more films, or any combination thereof, and the three-dimensional spacers can be present on any one of the aforementioned layers of material, where the spacers can be present on the layer of material's outer-facing surface, inner-facing surface, or both. The splash resistance, as measured by ASTM F1862-13, can be further enhanced if the materials in the multi-layered structure are hydrophobic, either naturally or through additives or treatments. This can reduce the potential for wicking of the fluid insult through the layers. Further, the three-dimensional spacers can be present on more than one of the layers of material in the multi-layered structure of the present invention. Moreover, the various layers of material used to form the multi-layered structure can each have basis weights ranging from about 10 gsm to about 150 gsm, such as from about 12.5 gsm to about 100 gsm, such as from about 15 gsm to about 80 gsm. For example, any meltblown material layers can have a basis weight ranging from about 10 gsm to about 75 gsm, such as from about 12.5 gsm to about 70 gsm, such as from about 15 gsm to about 50 gsm. Further, any spunlace or bicomponent nonwoven material layers can have a basis weight ranging from about 10 gsm to about 25 gsm, such as from about 12.5 gsm to about 20 gsm, such as from about 15 gsm to about 17.5 gsm. In addition, any spunbond material layers can have a basis weight ranging from about 15 gsm to about 60 gsm, such as from about 20 gsm to about 50 gsm, such as from about 20 gsm to about 45 gsm.

A spunbond web is one type of nonwoven material that can be used in one or more layers of the multi-layered structure of the present invention. A spunbond web is a material made from small diameter fibers which are formed by extruding molten thermoplastic material as filaments from a plurality of fine, usually circular capillaries of a spinneret with the diameter of the extruded filaments then being rapidly reduced as by, for example, in U.S. Pat. Nos. 4,340,563; 3,692,618; 3,802,817; 3,338,992; 3,341,394; 3,502,763; and 3,542,615. Spunbond fibers are generally not tacky when they are deposited onto a collecting surface. Spunbond fibers are generally continuous and have average diameters (from a sample of at least 10) larger than 7 microns, more particularly, between about 10 and 20 microns.

A meltblown web can also be used in one or more layers of the multi-layered structure of the present invention. A meltblown web is formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. The meltblown fibers are then carried by the high velocity gas stream and are deposited on a collecting surface to form a web of randomly dispersed meltblown fibers. Such a process is disclosed, for example, in U.S. Pat. No. 3,849,241. Meltblown fibers are microfibers which may be continuous or discontinuous, are generally smaller than 10 microns in average diameter, and are generally tacky when deposited onto a collecting surface.

A laminate of spunbond and meltblown material, (e.g., a spunbond/meltblown/spunbond (SMS) laminate) can also be used in one or more layers of the multi-layered structure of the present invention. Such a laminate and others are described in U.S. Pat. Nos. 4,041,203; 5,169,706; 5,145,727; 5,178,931; and 5,188,885. Such a laminate may be made by sequentially depositing onto a moving forming belt first a spunbond layer, then a meltblown layer and last another spunbond layer and then bonding the laminate in a manner described below. Alternatively, the layers may be made individually, collected in rolls, and combined in a separate bonding step. Such laminates usually have a basis weight of from about 0.1 to 12 osy (6 to 400 gsm), or more particularly from about 0.75 to about 3 osy. Multilayer laminates may also have various numbers of meltblown (abbreviated as "M") layers or multiple spunbond (abbreviated as "S") layers in many different configurations and may include other materials like films (abbreviated as "F") or coform materials (see U.S. Pat. No. 4,100,324 for descriptions of exemplary coform materials). Examples include SMMS laminates, SM laminates, SFS laminates, etc.

A hydroentangled web can also be used in one or more layers of the multi-layered structure of the present invention. Hydroentangled webs can also be used in one or more layers of the multi-layered structure of the present invention. A hydroentangled web is a web formed by a process wherein a nonwoven web, or layers of a non-woven web, are subjected to streams of a non-compressible fluid, e.g., water, at a high enough energy level and for a sufficient time to entangle the fibers thereof. The fluid may advantageously be used at a pressure of between about 200 and 5000 psig (14-351 $kg/cm^2$ gauge) from a distance of a few inches (centimeters) above the web while the web is supported by a mesh structure. This process is described in detail in U.S. Pat. No. 3,486,168. Nonwoven webs subjected to hydroentangling are referred to as, for example, spunlace materials.

A bonded carded web can also be used in one or more layers of the multi-layered structure of the present invention. A bonded carded web is a nonwoven web that is made from staple fibers which are sent through a combing or carding unit, which separates or breaks apart and aligns the staple fibers in the machine direction to form a generally machine direction-oriented fibrous nonwoven web. This material may be bonded together by methods that include point bonding, through air bonding, ultrasonic bonding, adhesive bonding, etc.

An airlaid web can also be used in one or more layers of the multi-layered structure of the present invention. An airlaid web is a nonwoven web formed by a process in which a fibrous nonwoven layer can be formed. In the airlaying process, bundles of small fibers having typical lengths ranging from about 3 to about 52 millimeters (mm) are separated and entrained in an air supply and then deposited onto a forming screen, usually with the assistance of a vacuum supply. The randomly deposited fibers then are bonded to one another using, for example, hot air or a spray adhesive. Airlaying is taught in, for example, U.S. Pat. No. 4,640,810.

Various layers made from elastomeric webs and foam webs are also contemplated for use in the multi-layered structure of the present invention.

The multi-layered structures of the present invention can also include one more layers of thin, breathable films that are commonly made from thermoplastic polyolefins like polyethylene and polypropylene and copolymers thereof because of their relatively low cost and ability to be processed. Polyethylene is generally used in the film production and when used in articles such as gowns or drapes, the film can be commonly "filled" with calcium carbonate, various kinds of clay, silica, alumina, barium carbonate, sodium carbonate, magnesium carbonate, talc, barium sulfate, magnesium sulfate, aluminum sulfate, titanium dioxide, zeolites, cellulose-type powders, kaolin, mica, carbon, calcium oxide, magnesium oxide, aluminum hydroxide, pulp powder, wood powder, cellulose derivatives, chitin and chitin derivatives, to increase breathability, while when used in articles such as masks, the film should be perforated or apertured to allow for the passage of air. Fillers produce microscopic pores in the film upon stretching to increase porosity. Unfortunately, these thin and breathable films are considered to be thermally sensitive because they have a tendency to become compromised by heat and/or or pressure. When these films are incorporated into laminate barrier materials by sandwiching them together with various combinations of other materials such as, for example, spunbond layers, meltblown layers and combinations thereof, the resulting laminate barrier materials are generally considered to be thermally sensitive as well. This characterization is particularly important for post-laminate formation processing steps. That is, manufacturing operations that convert the thermally sensitive barrier materials after such films are formed into the laminate barrier materials. For example, when thermally sensitive barrier materials are converted into gowns or other articles utilizing thermal point bonding and/or ultrasonic bonding techniques or when components such as, for example, tie cords or other features are attached to the articles, the breathable films of barrier laminate are frequently compromised such that they so longer provide desired levels of barrier to liquid penetration and pathogens. In one particular embodiment, the present invention provides for a multi-layered structure which incorporates a layer of material having a pattern or random distribution of three-dimensional spacers applied thereon. Such a layer improves the ability of the multi-layered structure to resist penetration by a splash of fluid by reducing the contact of adjacent layers of material and/or absorbing the energy produced by a fluid impact on the multi-layered structure, and/or providing for a mechanism by which fluid that strikes the multi-layered structure may be channeled away from the point of contact.

In another embodiment, one or more of the layers of the multi-layered structure, such as the inner layer, can be formed from a high opacity hydrophobic material. The use of such a material can further enhance the ability of the multi-layered structure to prevent fluids from passing through the inner layer and can help avoid the potential false positives (failures) in the ASTM F1862-13 test, which can happen with thin or translucent materials are used for the inner layer of the multi-layered structure. When such thin or translucent materials are used and the blood breaches the layer of material that is adjacent the inner layer, it can appear that all layers of the structure have been breached resulting in a failure per the ASTM F1862-13 method, even when a breach of the inner layer has not actually occurred.

Regardless of the particular materials used to form the two or more layers of the multi-layered structure contemplated by the present invention, the multi-layered structure can be formed into various articles of personal protective equipment including, but not limited to, face masks, surgical gowns, surgical drapes, surgical protective hoods/headwear, bouffant caps, and the like as discussed above.

III. Arrangement of the Three-Dimensional Spacers and Layer of Material

Figure 5:
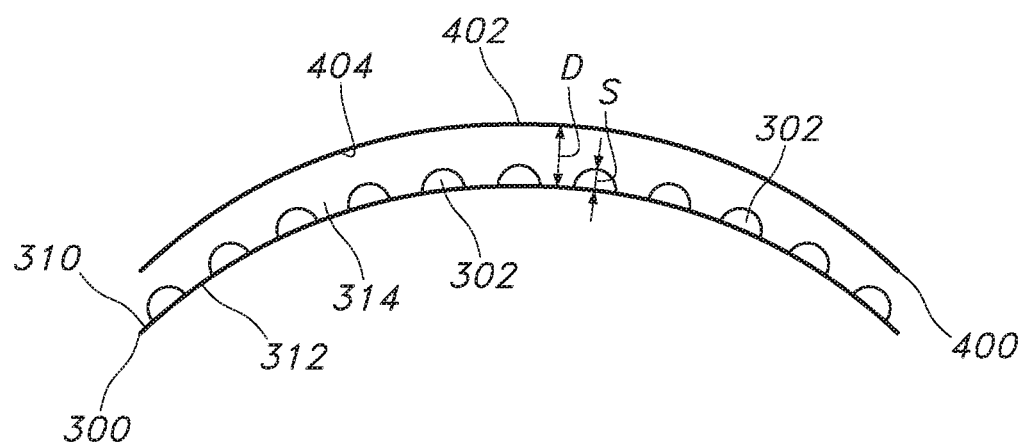
FIG. 5 is a cross-sectional view of two layers of the multi-layered structure of the present invention prior to an insult of a bodily fluid, such as blood, at an outer-facing surface of the multi-layered structure.
Figure 6:
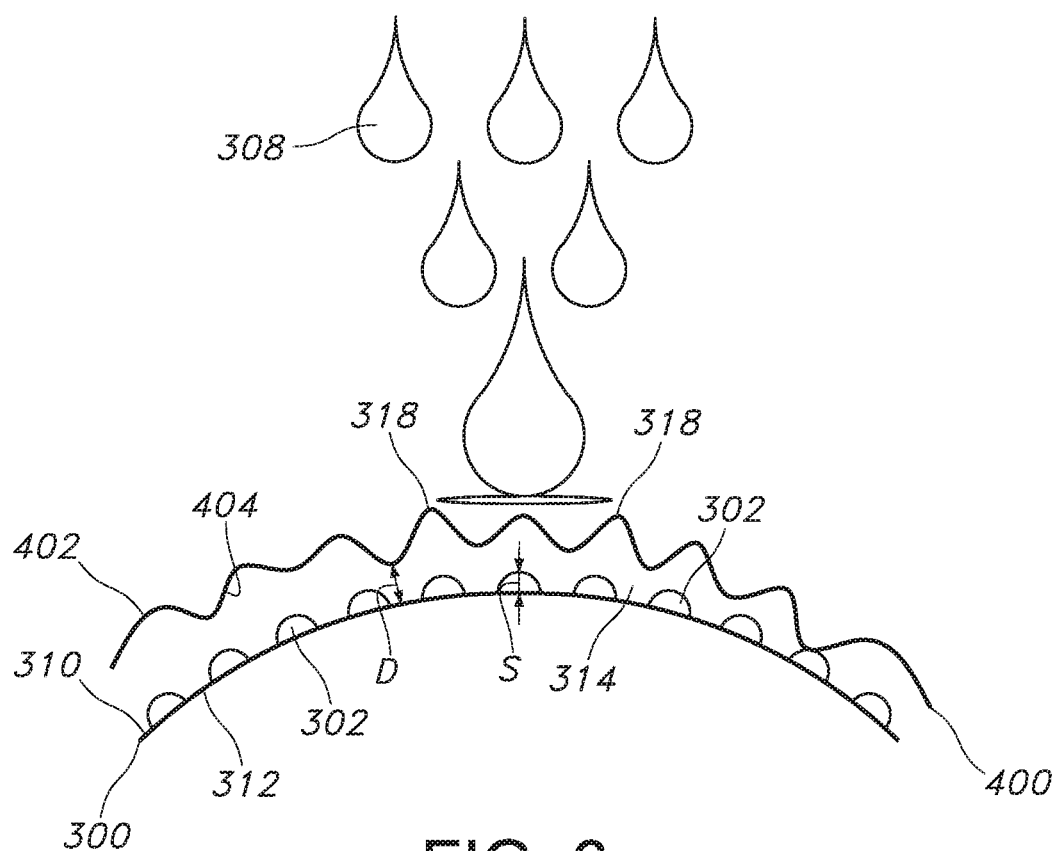
FIG. 6 is a cross-sectional view of two layers of the multi-layered structure of the present invention during an insult of a bodily fluid, such as blood, at an outer-facing surface of the multi-layered structure.

The three-dimensional spacers and layers of material discussed above can be arranged in various embodiments to form a multi-layered structure that improves splash resistance and can be employed in face masks, surgical gowns, surgical drapes, bouffant caps, and other PPE, where the forced separation of layers facilitated by the plurality of three-dimensional spacers enhances the splash resistance of the structure without the adding bulk, weight, and discomfort that occur when splash resistance is increased via the use of additional layers of material. Turning now to FIGS. 5 and 6, two layers of a multi-layered structure of the present invention are shown to demonstrate the functionality of the three-dimensional spacers when a fluid insult such is introduced to the multi-layered structure.

Specifically, FIG. 5 is a cross-sectional view of a multi-layered structure that includes an inner layer of material 300 and an outer layer of material 400 prior to an insult of a bodily fluid 308, such as blood, where the inner layer of material 300 is the layer closest to the skin of a user and the outer layer of material 400 is the layer furthest from the user when the structure is part of PPE such as a face mask, surgical gown, surgical drape, bouffant cap, etc. The inner layer of material 300 includes an outer-facing surface 310 and an inner-facing surface 312, while the outer layer of material 400 includes an outer-facing surface 402 and an inner-facing surface 404. A plurality of three-dimensional spacers 302 are disposed on the outer-facing surface 310 of the inner layer of material 300, and the three-dimensional spacers 302 have a maximum height S. The distance D between the outer-facing surface 310 of the inner layer of material 300 and the inner-facing surface 404 of the outer layer of material 400 is at least as large as the maximum height S, where the maximum height S of the three-dimensional spacers 302 forces separation between the inner layer of material 300 and the outer layer of material 400. Such an arrangement enhances the fluid barrier and splash resistance of the multi-layered structure of the present invention. In particular, the separation between the layers helps to reduce the area of contact between the layers and thus lowers the ability of fluid to transfer from one layer to the next. As such, the three-dimensional spacers 302 therefore help to separate the layers of material 300 and 400 such that fluid cannot be as easily transferred through the layers by decreasing the area of surface contact between the layers.

Further, the three-dimensional spacers 302 define channels 314 that are located adjacent the a surface of a layer of material on which the three-dimensional spacers 302 are disposed, which happens to be the outer-facing surface 310 of the inner layer 300 in the particular multi-layered structure of FIG. 5, although it is to be understood that the three-dimensional spacers 302 and channels 314 can be present on an inner or outer-facing surface of any layer. By providing the channels 314, a fluid insult may be transferred and more uniformly distributed across a layer when the layer is contacted with the fluid insult. This separation also provides for a contained space in which the fluid can easily flow laterally when the layers are compressed, which also helps prevent the fluid from transferring through the layers. This distribution of fluid helps to prevent the accumulation of a pool of fluid at a particular location on the outer surface of a layer. It is typically the case that fluid which is heavily concentrated at a particular location on a layer of the multi-layered structure is more likely to be transferred through that layer of the multi-layered structure, as opposed to the situation in which the same amount of fluid were distributed over a larger portion of the outer surface of the layer. The channels 314 may be interconnected channels such that all of the channels 314 are in communication with one another. This allows for the advantage of having fluid which contacts a layer at any point of contact 318 to be distributed through a larger number of channels 314. Alternatively, the channels 314 may be configured such that only a portion of the channels 314 are in communication with one another. Further, the channels 314 may be provided in any number in accordance with other exemplary embodiments of the present invention. The channels 314 may thus redirect fluid which contacts a layer to a desired location. For instance, the channels 314 may be configured such that fluid which engages a layer of material at the point of contact 318 is redirected along the outer surface that layer and flows through the multi-layered structure to a position along, for instance, the edge of the multi-layered structure.

FIG. 6 shows the functionality of the three-dimensional spacers 302 and channels 314 during an insult of a bodily fluid 308. As shown, the three-dimensional spacers 302 are configured such that their three-dimensional structure enables the outer layer of material 400 to flex and absorb at least a portion of the forces transmitted by the fluid 308 striking the outer-facing surface 402 of the outer layer of material 400 without allowing the inner-facing surface 404 to contact the outer-facing surface 310 of the inner layer of material 300. In this regard, the presence of the three-dimensional spacers 302 having a maximum height S results in the space between the inner-facing surface 404 of the outer layer of material 400 and the outer-facing surface 310 of the inner layer of material 300 having a distance D that is at least as large as the maximum height S. Absorption of the aforementioned forces imparted by a fluid strike may help to prevent fluid from penetrating past the inner layer of material 300 of the multi-layered structure of the present invention. In this regard, it may be the case that fluid is already trapped between one or more layers of the multi-layered structure of the present invention. Forces imparted by the fluid 308 striking the multi-layered structure cause these already trapped fluids to be pushed further through the multi-layered structure. However, due to the formation of a plurality of channels 314 as a result of the forced separation between the layers 300 and 400 created by the presence of the three-dimensional spacers 302, these trapped fluids can be prevented from propagating through the inner most layers of the multi-layered structure and contacting the skin or the user of PPE formed from the multi-layered structure of the present invention.

As stated, the various multi-layered structures contemplated by the present invention and shown in FIGS. 8-12 may be composed of two or more of layers 802, 804, 806, and 808. The arrangement of the layers 802, 804, 806, and 808 may be modified such that any combination of sequencing is possible and such that anywhere from two to four layers can be utilized, where the four-layered structures 800, 860, and 870, and the three-layered structures 880 and 890 represent some of the particular embodiments contemplated by the present invention. Further, it should be understood that the outer layer 802, middle layers 804 and 806, and the inner layer 808 may be made of the same materials or different materials. In addition, a plurality of three-dimensional spacers can be applied to the inner-facing surface, the outer-facing surface, or both of any of the layers of material 802, 804, 806, and 808. Moreover, additional layers other than those shown in the figures may also be incorporated into the multi-layered structure to achieve the desired properties, although the present inventors have found that sufficient splash resistance can be achieved with the use of fewer layers than taught in the art, which is due, at least in part, to the incorporation of the three-dimensional spacers 302 into the various multi-layered structures 800, 860, 870, 880, and 890. The additional layers may be constructed from various materials known to those skilled in the art such as those described above. Specific embodiments of the multi-layered structure construction are discussed in more detail below, although it is to be understood that the present invention contemplates any other suitable arrangement of multiple layers of material where a plurality of three-dimensional spacers are applied to one or both surfaces of any of the multiple layers of material.

Figure 8:
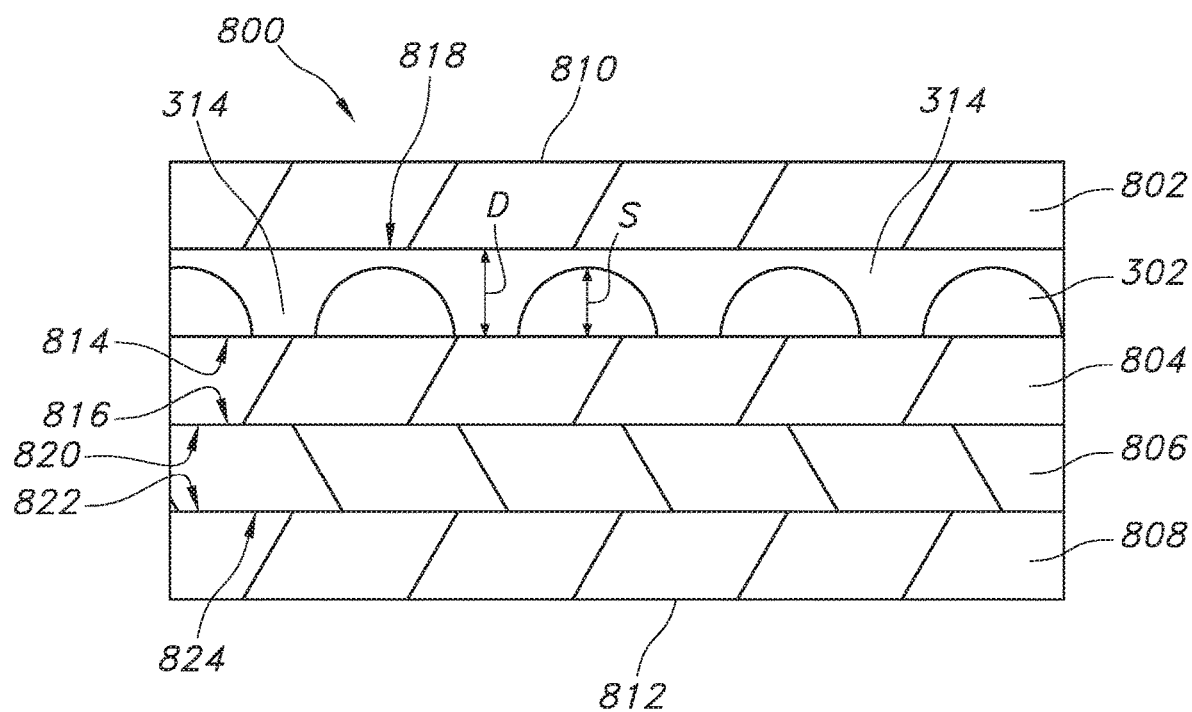
FIG. 8 is a cross-sectional view of an exemplary multi-layered structure that contains three-dimensional spacers applied to one of the layers of the multi-layered structure according to one embodiment of the present invention.

Turning now to FIG. 8, a four-layered structure 800 is illustrated according to one embodiment of the present invention. The multi-layered structure 800 has four layers including an outer layer of material 802 and an inner layer of material 808, where the outer layer of material 802 includes an outer-facing surface 810 and an inner-facing surface 818, and the inner layer of material 808 includes an outer-facing surface 824 and an inner-facing surface 812. Disposed between the outer layer of material 802 and the inner layer of material 808 are a layer of material 804 and a layer of material 806. The layer of material 804 is positioned adjacent the outer layer of material 802 and includes an outer-facing surface 814 and an inner-facing surface 816. Meanwhile, the layer of material 806 is positioned adjacent the inner layer of material 808 and includes an outer-facing surface 820 and an inner-facing surface 822. As shown in FIG. 8, a plurality of three-dimensional spacers 302 are disposed on the outer-facing surface 814 of the layer of material 804, which, in this particular embodiment, can also be referred to as the second layer of material present past the outer-facing surface 810 of the outer layer of material 802, which also serves as the outer-facing surface of the entire multi-layered structure. The plurality of three-dimensional spacers 302 define a plurality of channels 314 that are formed between the outer layer of material 802 and the layer of material 804. Further, the plurality of three-dimensional spacers 302 create a forced separation or space between the outer-facing surface 814 of the second layer of material 804 and the inner-facing surface 818 of the first (or outermost) layer of material 802. The separation between the outer-facing surface 814 of the second layer of material 804 and the inner-facing surface 818 of the first layer of material 802 spans a distance D, which is controlled at least in part by the maximum height S of the three-dimensional spacers 302. In the specific embodiment of FIG. 8, the outer (first) layer of material 802, the second layer of material 804 on which the three-dimensional spacers 302 are disposed, and the inner (fourth) layer of material 808 are spunbond webs, while the third layer of material 806 positioned adjacent the inner layer of material 808 is a meltblown web. Further, in the specific embodiment of FIG. 8, the three-dimensional spacers 302 are formed from a binder which contains an encapsulated phase change material.

The multi-layered structure 800 was tested for splash resistance according to ASTM Standard F-1862 (Level 3), where the fluid was prevented from passing through the three-dimensional spacers 302 present on the outer-facing surface 814 of the spunbond layer of material 804, which is the second layer past the point of fluid contact at the outer-facing surface 810 of the outer layer of material 802. In other words, the multi-layered structure 800 of FIG. 8 required only two layers of material (e.g., spunbond layer 802 and spunbond layer 804 having the three-dimensional spacers 302 present on its outer-facing surface 814) to prevent passage of fluid through the multi-layered structure.

Figure 9:
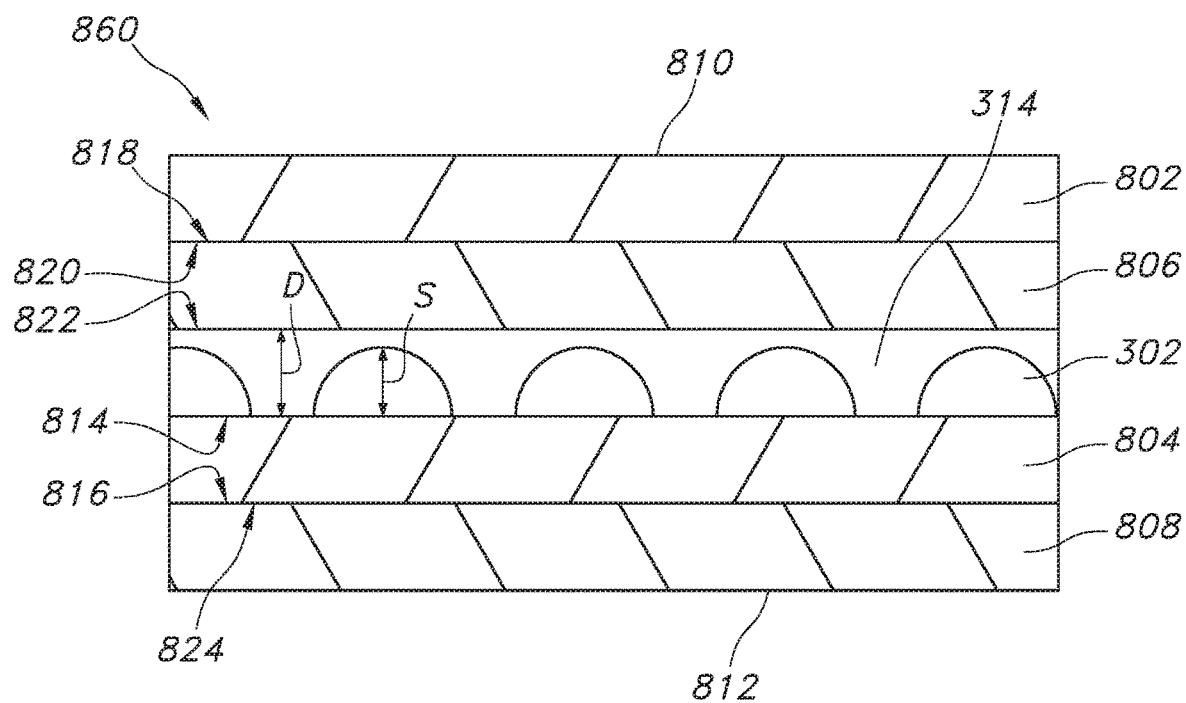
FIG. 9 is a cross-sectional view of an exemplary multi-layered structure that contains three-dimensional spacers applied to one of the layers of the multi-layered structure according to another embodiment of the present invention.

Next, FIG. 9 shows another four-layered structure 860 according to another embodiment of the present invention. The multi-layered structure 860 has four layers including an outer layer of material 802 and an inner layer of material 808, where the outer layer of material 802 includes an outer-facing surface 810 and an inner-facing surface 818, and the inner layer of material 808 includes an outer-facing surface 824 and an inner-facing surface 812. Disposed between the outer layer of material 802 and the inner layer of material 808 are a layer of material 806 and a layer of material 804. The layer of material 806 is positioned adjacent the outer layer of material 802 and includes an outer-facing surface 820 and an inner-facing surface 822. Meanwhile, the layer of material 804 is positioned adjacent the inner layer of material 808 and includes an outer-facing surface 814 and an inner-facing surface 816. As shown in FIG. 9, a plurality of three-dimensional spacers 302 are disposed on the outer-facing surface 814 of the layer of material 804, which, in this particular embodiment, can also be referred to as the third layer of material present past the outer-facing surface 810 of the outer layer of material 802, which also serves as the outer-facing surface of the entire multi-layered structure. The plurality of three-dimensional spacers 302 define a plurality of channels 314 that are formed between the layer of material 806 and the layer of material 804. Further, the plurality of three-dimensional spacers 302 create a forced separation or space between the outer-facing surface 814 of the third layer of material 804 and the inner-facing surface 822 of the second layer of material 806. The separation between the outer-facing surface 814 of the third layer of material 804 and the inner-facing surface 822 of the second layer of material 806 spans a distance D, which is controlled at least in part by the maximum height S of the three-dimensional spacers 302. In the specific embodiment of FIG. 9, the outer (first) layer of material 802, the third layer of material 804 on which the three-dimensional spacers 302 are disposed, and the inner (fourth) layer of material 808 are spunbond webs, while the second layer of material 806 positioned adjacent the outer layer of material 802 is a meltblown web. Further, in the specific embodiment of FIG. 9, the three-dimensional spacers 302 are formed from a binder which contains an encapsulated phase change material.

The multi-layered structure 860 was tested for splash resistance according to ASTM Standard F-1862 (Level 3), where the fluid did pass through the three-dimensional spacers 302 present on the outer-facing surface 814 of the spunbond layer of material 804, which in the specific multi-layered structure 860 is the third layer past the point of fluid contact at the outer-facing surface 810 of the outer layer of material 802. However, the fluid did not pass through the entire multi-layered structure. In other words, the multi-layered structure 860 of FIG. 9 required three layers of material (e.g., spunbond layer 802, meltblown layer 806, and spunbond layer 804 having the three-dimensional structures 302 present on its outer-facing surface 814) to prevent passage of fluid through the multi-layered structure. Comparing the multi-layered structure 800 of FIG. 8 to the multi-layered structure 860 of FIG. 9, it appears that the three-dimensional spacers 302 provide better splash resistance when positioned immediately adjacent a spunbond layer or any layer other than a meltblown layer that catches a majority of the initial fluid insult. The present inventors hypothesize that this may be the case because the three-dimensional spacers are configured in such an arrangement have more room between the layers and can repel the initial pressure of the fluid insult, after which the layers exposed to the fluid insult are positioned closer to each other, resulting the fluid absorbing through the layers.

Figure 10:
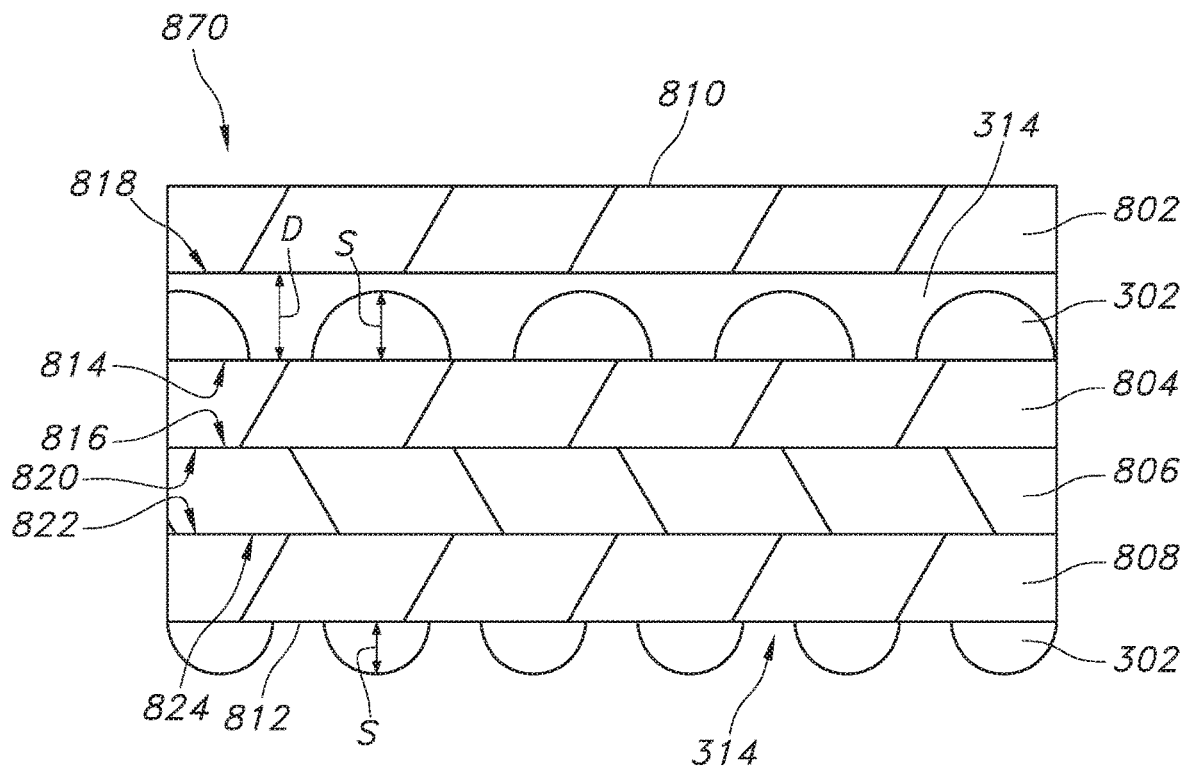
FIG. 10 is a cross-sectional view of an exemplary multi-layered structure that contains three-dimensional spacers applied to two of the layers of the multi-layered structure according to still another embodiment of the present invention.

In addition, FIG. 10 illustrates a four-layered structure 870 according to one more embodiment of the present invention. The multi-layered structure 870 has four layers including an outer layer of material 802 and an inner layer of material 808, where the outer layer of material 802 includes an outer-facing surface 810 and an inner-facing surface 818, and the inner layer of material 808 includes an outer-facing surface 824 and an inner-facing surface 812. Disposed between the outer layer of material 802 and the inner layer of material 808 are a layer of material 804 and a layer of material 806. The layer of material 804 is positioned adjacent the outer layer of material 802 and includes an outer-facing surface 814 and an inner-facing surface 816. Meanwhile, the layer of material 806 is positioned adjacent the inner layer of material 808 and includes an outer-facing surface 820 and an inner-facing surface 822.

As shown in FIG. 10, a plurality of three-dimensional spacers 302 are disposed on the outer-facing surface 814 of the layer of material 804, which, in this particular embodiment, can also be referred to as the second layer of material present past the outer-facing surface 810 of the outer layer of material 802, which also serves as the outer-facing surface of the entire multi-layered structure. The plurality of three-dimensional spacers 302 define a plurality of channels 314 that are formed between the outer layer of material 802 and the layer of material 804. Further, the plurality of three-dimensional spacers 302 create a forced separation or space between the outer-facing surface 814 of the second layer of material 804 and the inner-facing surface 818 of the first (or outermost) layer of material 802. The separation between the outer-facing surface 814 of the second layer of material 804 and the inner-facing surface 818 of the first layer of material 802 spans a distance D, which is controlled at least in part by the maximum height S of the three-dimensional spacers 302. In addition, a plurality of three-dimensional spacers 302 are also disposed on the inner-facing surface 812 of the inner layer of material 808, where the three-dimensional spacers 302 also define a plurality of channels 314. Further, the plurality of three-dimensional spacers 302 present on the inner-facing surface 812 of the inner layer of material 808 can create a forced separation between a user's skin and the inner layer of material 808 to provide for added comfort to the user since the multi-layered structure 870 only contacts the user at the three-dimensional spacers 302 rather than across the entire inner-facing surface 812 as in multi-layered structures 800 and 860. The separation is controlled at least in part by the maximum height S of the three-dimensional spacers 302.

In the specific embodiment of FIG. 10, the outer (first) layer of material 802, the second layer of material 804 on which a plurality of three-dimensional spacers 302 are disposed, and the inner (fourth) layer of material 808 are spunbond webs, while the third layer of material 806 positioned adjacent the inner layer of material 808 is a melt-blown web. Further, in the specific embodiment of FIG. 10, the three-dimensional spacers 302 present on the outer-facing surface 814 of the second layer of material 804 are in the form of an acrylic binder, while the three-dimensional spacers 302 present on the inner-facing surface 812 of the inner layer 808 are formed from a binder which contains an encapsulated phase change material so that the three-dimensional spacers 302 present on the inner-facing surface 812 not only minimize the degree of contact between the multi-layered structure 870 and the user, but can also facilitate additional cooling to the user.

The multi-layered structure 870 was tested for splash resistance according to ASTM Standard F-1862 (Level 3), where the fluid was prevented from passing through the three-dimensional spacers 302 present on the outer-facing surface 814 of the spunbond layer of material 804, which is the second layer past the point of fluid contact at the outer-facing surface 810 of the outer layer of material 802. In other words, the multi-layered structure 870 of FIG. 10 required only two layers of material (e.g., spunbond layer 802 and spunbond layer 804 having the three-dimensional spacers 302 present on its outer-facing surface 814) to prevent passage of fluid through the multi-layered structure.

Figure 11:
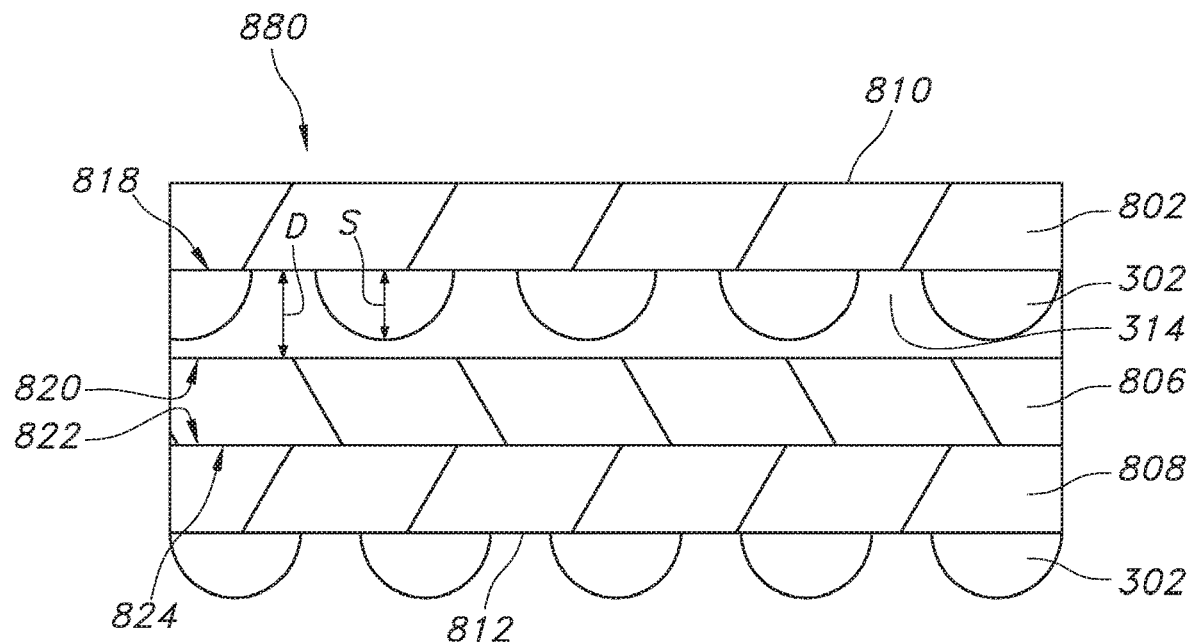
FIG. 11 is a cross-sectional view of an exemplary multi-layered structure that contains three-dimensional spacers applied to two of the layers of the multi-layered structure according to one embodiment of the present invention.

Meanwhile, FIG. 11 shows a three-layered structure 880 according to an additional embodiment of the present invention in which the spunbond layer 804 has been eliminated. The multi-layered structure 880 has three layers including an outer (first) layer of material 802 and an inner (third) layer of material 808, where the outer (first) layer of material 802 includes an outer-facing surface 810 and an inner-facing surface 818, and the inner (third) layer of material 808 includes an outer-facing surface 824 and an inner-facing surface 812. Disposed between the outer (first) layer of material 802 and the inner (third) layer of material 808 is a second layer of material 806. The second layer of material 806 includes an outer-facing surface 820 and an inner-facing surface 822.

As shown in FIG. 11, a plurality of three-dimensional spacers 302 are disposed on the inner-facing surface 818 of the outer layer of material 802, which is also referred to as the first layer of material and the outer-facing surface of the entire multi-layered structure. The plurality of three-dimensional spacers 302 define a plurality of channels 314 that are formed between the outer (first) layer of material 802 and the second layer of material 806. Further, the plurality of three-dimensional spacers 302 create a forced separation or space between the inner-facing surface 818 of the outer (first) layer of material 802 and the outer-facing surface 820 of the second layer of material 806. The separation between the outer-facing surface 820 of the second layer of material 806 and the inner-facing surface 818 of the outer (first) layer of material 802 spans a distance D, which is controlled at least in part by the maximum height S of the three-dimensional spacers 302. In addition, a plurality of three-dimensional spacers 302 are also disposed on the inner-facing surface 812 of the inner (third) layer of material 808, where the three-dimensional structures 302 also define a plurality of channels 314. Further, the plurality of three-dimensional spacers 302 present on the inner-facing surface 812 of the inner (third) layer of material 808 can create a forced separation between a user's skin and the inner (third) layer of material 808 to provide for added comfort to the user since the multi-layered structure 880 only contacts the user at the three-dimensional spacers 302 rather than across the entire inner-facing surface 812 as in the multi-layered structures 800 and 860. The separation is controlled at least in part by the maximum height S of the three-dimensional spacers 302.

In the specific embodiment of FIG. 11, the outer (first) layer of material 802 on which a plurality of three-dimensional spacers 302 are disposed and the inner (third) layer of material 808 are spunbond webs, while the second layer of material 806 positioned between them is a meltblown web. Further, in the specific embodiment of FIG. 11, the three-dimensional spacers 302 present on the inner-facing surface 818 of the (outer) first layer of material 802 are in the form of an acrylic binder, while the three-dimensional spacers 302 present on the inner-facing surface 812 of the inner (third) layer 808 are formed from a binder which contains an encapsulated phase change material so that the three-dimensional spacers 302 present on the inner-facing surface 812 not only minimize the degree of contact between the multi-layered structure 880 and the user, but can also facilitate additional cooling to the user.

The multi-layered structure 880 was tested for splash resistance according to ASTM Standard F-1862 (Level 3), where the fluid was prevented from passing through the meltblown (second) layer 806 due at least in part to the presence of three-dimensional spacers 302 present on the inner-facing surface 818 of the spunbond outer (first) layer of material 802, which corresponds with the outermost layer of the multi-layered structure 880. In other words, the multi-layered structure 880 of FIG. 11 required only two layers of material (e.g., spunbond layer 802 having the three-dimensional spacers 302 present on its inner-facing surface 818 and meltblown layer 808) to prevent passage of fluid through the multi-layered structure, even though the multi-layered structure 880 was only three-layered.

Figure 12:
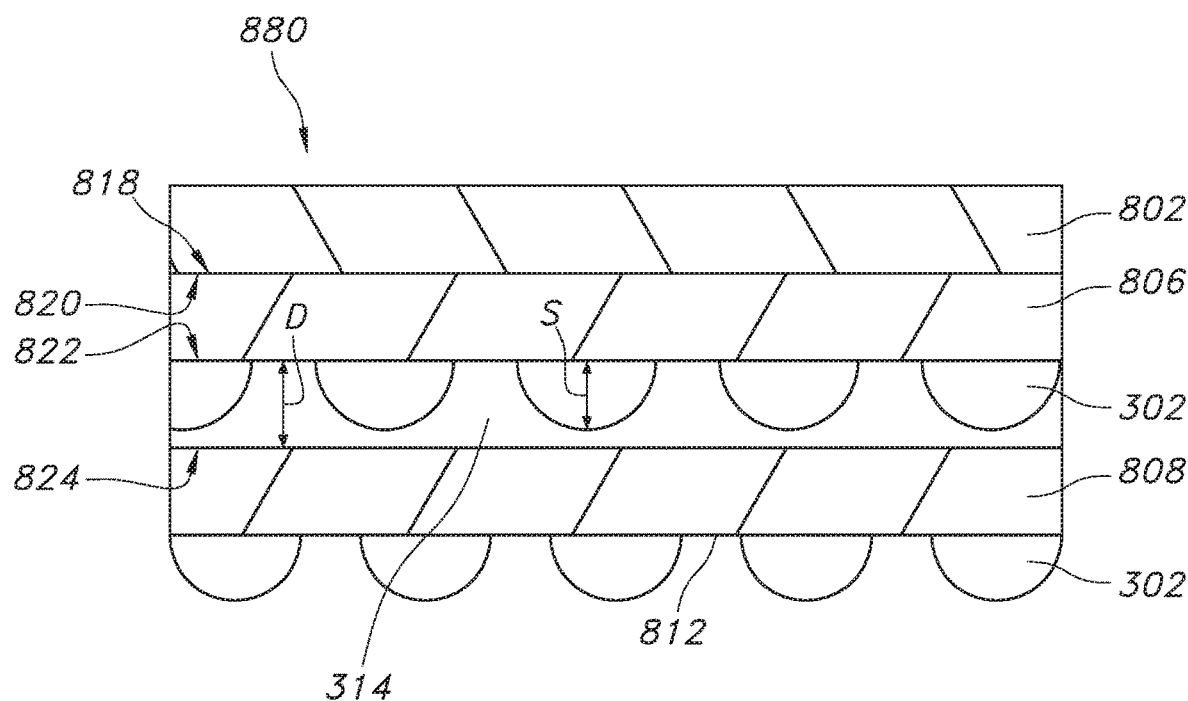
FIG. 12 is a cross-sectional view of an exemplary multi-layered structure that contains three-dimensional spacers applied to two of the layers of the multi-layered structure according to one embodiment of the present invention.

Further, FIG. 12 illustrates a three-layered structure 890 according to yet another embodiment of the present invention in which the spunbond layer 804 has been eliminated. The multi-layered structure 890 has three layers including an outer (first) layer of material 802 and an inner (third) layer of material 808, where the outer (first) layer of material 802 includes an outer-facing surface 810 and an inner-facing surface 818, and the inner (third) layer of material 808 includes an outer-facing surface 824 and an inner-facing surface 812. Disposed between the outer (first) layer of material 802 and the inner (third) layer of material 808 is a second layer of material 806. The layer of material 806 includes an outer-facing surface 820 and an inner-facing surface 822.

As shown in FIG. 12, a plurality of three-dimensional spacers 302 are disposed on the inner-facing surface 822 of the second layer of material 806. The plurality of three-dimensional spacers 302 define a plurality of channels 314 that are formed between the second layer of material 806 and the inner (third) layer of material 808. Further, the plurality of three-dimensional spacers 302 create a forced separation or space between the inner-facing surface 822 of the second layer of material 806 and the outer-facing surface 824 of the inner (third) layer of material 808. The separation between the inner-facing surface 822 of the second layer of material 806 and the outer-facing surface 824 of the inner (third) layer of material 808 spans a distance D, which is controlled at least in part by the maximum height S of the three-dimensional spacers 302. In addition, a plurality of three-dimensional spacers 302 are also disposed on the inner-facing surface 812 of the inner (third) layer of material 808, where the three-dimensional spacers 302 also define a plurality of channels 314. Further, the plurality of three-dimensional spacers 302 present on the inner-facing surface 812 of the inner (third) layer of material 808 can create a forced separation between a user's skin and the inner (third) layer of material 808 to provide for added comfort to the user since the multi-layered structure 890 only contacts the user at the three-dimensional spacers 302 rather than across the entire inner-facing surface 812 as in the multi-layered structures 800 and 860. The separation is controlled at least in part by the maximum height S of the three-dimensional spacers 302.

In the specific embodiment of FIG. 12, the outer (first) layer of material 802 and the inner (third) layer of material 808 are spunbond webs, while the second layer of material 806 positioned between them and on which a plurality of three-dimensional spacers 302 are disposed is a meltblown web. Further, in the specific embodiment of FIG. 12, the three-dimensional spacers 302 present on the inner-facing surface 822 of the second layer of material 806 are in the form of an acrylic binder, while the three-dimensional spacers 302 present on the inner-facing surface 812 of the inner (third) layer 808 are formed from a binder which contains an encapsulated phase change material so that the three-dimensional spacers 302 present on the inner-facing surface 812 not only minimize the degree of contact between the multi-layered structure 890 and the user, but can also facilitate additional cooling to the user.

The multi-layered structure 890 was tested for splash resistance according to ASTM Standard F-1862 (Level 3), where the fluid was prevented from passing through the meltblown (second) layer 806 due at least in part to the presence of three-dimensional spacers 302 present on the inner-facing surface 822 of the meltblown (second) layer of material 806. However, the splash resistance was not as good as that shown for the multi-layered structure 880. In any event, the multi-layered structure 890 of FIG. 12 still required only two layers of material (e.g., spunbond layer 802 and meltblown layer 806 having the three-dimensional spacers 302 present on its inner-facing surface 822) to prevent passage of fluid through the multi-layered structure, even though the multi-layered structure 890 was only three-layered.

Figure 7:
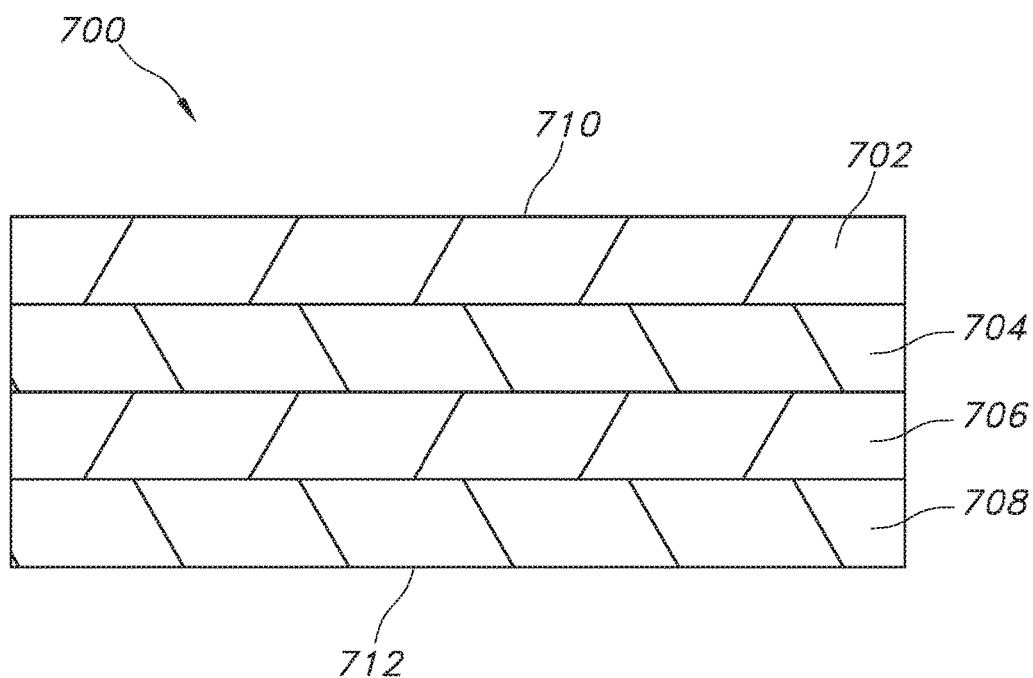
FIG. 7 is a cross-sectional view of a multi-layered structure that does not contain the three-dimensional spacers contemplated by the present invention.

For comparison, FIG. 7 shows a four-layered structure 700 that does not include the three-dimensional spacers of the multi-layered structures of the present invention. The multi-layered structure 700 has an outer layer of material 702 having an outer-facing surface 710 and an inner layer of material 708 having an inner-facing surface 712, where the outer layer of material 702 is positioned furthest from the user and the inner layer of material 708 is positioned closest to the user, such as next to the skin. Between the outer layer of material 702 and the inner layer of material 708 are two additional layers 704 and 706. The layer of material 704 is adjacent the outer layer of material 702, while the layer of material 706 is adjacent the inner layer of material 708. The outer layer of material 702, the inner layer of material 708, and the layer of material 704 adjacent the outer layer of material 702 can each be formed from a spunbond web, while the layer of material 706 adjacent the inner layer of material 708 can be a meltblown material. However, it is to be understood that any of the types of nonwoven web, foam, or film materials can be used to form such layers.

In any event, the multi-layered structure 700 was tested for splash resistance according to ASTM Standard F-1862 (Level 3), where the fluid was prevented from passing through the layer of material 706, which is the third layer past the point of fluid contact at the outer-facing surface 710 of the outer layer of material 702, meaning that the multi-layered structure 700 of FIG. 7 required three layers (e.g., two spunbond layers 702, 704 and a meltblown layer 706) to prevent passage of fluid through the multi-layered structure 700. In contrast, the multi-layered structures of the present invention can prevent the passage of fluid therethrough utilizing only one layer of material and the three-dimensional spacers discussed above, particularly when the three-dimensional spacers are adjacent a spunbond layer in the direction of the outer-facing surface or point of fluid contact.

In general, comparing FIGS. 8-12 with FIG. 7 shows that incorporating three-dimensional spacers on a layer of a three-layered structure or a four-layered structure can increase the splash resistance of such a structure so long as the three-dimensional spacers are postioned within the multi-layered structure (e.g., not on the outer-facing surface of the outer layer or the inner-facing surface of the inner layer).

The present invention may be better understood with reference to the following examples.

Example 1

In Example 1, a multi-layered structure generally corresponding to the arrangement shown in FIG. 9 (Control Sample) but without the three-dimensional spaces 302 was compared to a multi-layered structure arranged as shown in FIG. 9 (Test Sample) for their ability to achieve Level 3 performance, which is the most stringent level of testing in ASTM F2100-11, where a face mask must resist splashes of 2 milliliters of synthetic blood (available from Johnson, Moen & Co., 2505 Northridge Lane NE, Rochester, Minn. 55906) at 160 mmHg per the ASTM F1862-13 procedure. In other words, the control sample included the four-layered structure 860 except for the three-dimensional spacers 302. The control sample multi-layered structure had an outer layer of material 802 formed from a polyester pulp wetlaid material having a basis weight of 0.5 ounces per square yard (16.95 gsm) and having an outer-facing surface 810. The control sample multi-layered structure 860 also included an inner layer of material 808 formed from a bicomponent carded nonwoven material having a basis weight of 0.5 ounces per square yard (16.95 gsm) and having an inner-facing surface 812, where the outer layer of material 802 was positioned closest to the fluid insult and the inner layer of material 808 was positioned furthest from the fluid insult, such as would be the case if the structure was used in a face mask worn next to the skin. Between the outer layer of material 802 and the inner layer of material 808 were two additional layers 804 and 806. The layer of material 806 was positioned adjacent the outer layer of material 802 and was formed from a meltblown material having a basis weight of 0.6 ounces per square yard (20.34 gsm), while the layer of material 804 was positioned adjacent the inner layer of material 808 and was formed from a spunbond material having a basis weight of 0.9 ounces per square yard (30.52 gsm).

Meanwhile, the test sample generally corresponded with the multi-layered structure 860 of FIG. 9. In particular, the test sample included an outer layer of material 802 formed from a polyester pulp wetlaid material having a basis weight of 0.5 ounces per square yard (16.95 gsm) and an inner layer of material 808 formed from a bicomponent carded nonwoven material having a basis weight of 0.5 ounces per square yard (16.95 gsm), where the outer layer of material 802 included an outer-facing surface 810 and an inner-facing surface 818, and the inner layer of material 808 included an outer-facing surface 824 and an inner-facing surface 812. Disposed between the outer layer of material 802 and the inner layer of material 808 were a layer of material 806 and a layer of material 804. The layer of material 806 was positioned adjacent the outer layer of material 802 and was formed from a meltblown material having a basis weight of 0.6 ounces per square yard (20.34 gsm), where the layer of material 806 included an outer-facing surface 820 and an inner-facing surface 822. Meanwhile, the layer of material 804 was positioned adjacent the inner layer of material 808 and was formed from a spunbond material having a basis weight of 0.9 ounces per square yard (30.52 gsm), where the layer of material 804 included an outer-facing surface 814 and an inner-facing surface 816. As shown in FIG. 9, a plurality of three-dimensional spacers 302 (i.e., dots) formed from an acrylic binder were also disposed on the outer-facing surface 814 of the layer of material 804, which is also referred to as the third layer of material present past the outer-facing surface 810 of the outer layer of material 802. The plurality of three-dimensional spacers 302 formed a plurality of channels 314 between the layer of material 806 and the layer of material 804. Further, the plurality of three-dimensional spacers 302 created a forced separation or space between the outer-facing surface 814 of the third layer of material 804 and the inner-facing surface 822 of the second layer of material 806.

The control sample and the test sample as described above were tested for splash resistance according to ASTM Standard F-1862 (Level 3), where the fluid passed through to the layer 808 in the Control Sample, meaning that the control sample failed ASTM Standard F-1862 (Level 3). However, the fluid did not pass through the layer 808 in the test sample, and thus the test sample passed ASTM Standard F-1862 (Level 3).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A splash resistant multi-layered structure, the multilayered structure comprising:
    an outer layer of material having an outer-facing surface and an inner-facing surface;
    an inner layer of material having an outer-facing surface and an inner-facing surface; and
    a first plurality of three-dimensional spacers disposed on a surface within the multi-layered structure, wherein the first plurality of three-dimensional spacers define a space between the outer layer of material and the inner layer of material, wherein the space spans a distance at least as great as a maximum height of the first plurality of three-dimensional spacers, further wherein the first plurality of three-dimensional spacers aid in absorbing energy associated with a fluid contacting the outer layer of material, wherein the first plurality of three-dimensional spacers comprises a binder and an encapsulated functional additive contained within the binder, wherein the encapsulated functional additive further comprises a phase change material; and
    a second plurality of three-dimensional spacers, wherein the second plurality of three-dimensional spacers are disposed on the inner-facing surface of the inner layer of material, wherein the second plurality of three-dimensional spacers define a space between the inner-facing surface and a user.

2. The multi-layered structure of claim 1, wherein the first plurality of three-dimensional spacers define a first plurality of channels for redirecting the flow of fluid that strikes the outer layer of material, wherein the channels have an orientation such that the fluid is directed laterally away from the point of contact of the fluid through the channels.

3. The multi-layered structure of claim 1, wherein the first plurality of three-dimensional spacers are arranged in a pattern.

4. The multi-layered structure of claim 3, wherein the pattern is continuous or discontinuous.

5. The multi-layered structure of claim 4, wherein the pattern comprises a plurality of dots, wherein the dots are arranged on a layer of material in a series of columns and a series of rows.

6. The multi-layered structure of claim 1, wherein the first plurality of three-dimensional spacers further comprise an ink.

7. The multi-layered structure of claim 1, wherein the binder is an acrylic binder.

8. The multi-layered structure of claim 6, wherein the ink is an elastic or non-elastic expandable ink.

9. The multi-layered structure of claim 1, wherein the encapsulated functional additive further comprises a fragrance, an absorbent material, a superabsorbent material, an antimicrobial, a therapeutic agent, a topical ointment, or a combination thereof.

10. The multi-layered structure of claim 1, wherein the functional additive is present in an amount ranging from about 0.25 wt % to about 70 wt. % based on the dry weight of the first plurality of three-dimensional spacers present within the multi-layered, structure.

11. The multi-layered structure of claim 1, wherein the multi-layered structure further comprises an additional layer of material disposed between the outer layer of material and the inner layer of material.

12. The multi-layered structure of claim 11, wherein the first plurality of three-dimensional spacers are disposed on an outer-facing surface of the additional layer of material.

13. The multi-layered structure of claim 12, wherein the additional layer of material is a spunbond web positioned adjacent the outer layer of material, wherein the multi-layered structure further comprises a meltblown web, wherein the meltblown web is positioned adjacent the inner layer of material.

14. The multi-layered structure of claim 11, wherein the additional layer of a material is a meltblown web.

15. The multi-layered structure of claim 14, wherein the first plurality of three-dimensional spacers are disposed on the inner-facing surface of the outer layer of material.

16. The multi-layered structure of claim 14, wherein the first plurality of three-dimensional spacers are disposed on an inner-facing surface of the meltblown web.

17. The multi-layered structure of claim 15, wherein the first plurality of three-dimensional spacers comprise an acrylic binder and the second plurality of three-dimensional spacers comprise a phase change material encapsulated within an acrylic binder.

18. The multi-layered structure of claim 1, wherein the outer layer of material and the inner layer of material each comprise a spunbond web.

19. An article formed from the multi-layered structure of claim 1, wherein the article is a face mask, a surgical gown, a surgical drape, a surgical hood, or a bouffant cap.

* * * * *